United States Patent
Kozloski et al.

(10) Patent No.: US 11,177,039 B2
(45) Date of Patent: Nov. 16, 2021

(54) ASSESSING A TREATMENT SERVICE BASED ON A MEASURE OF TRUST DYNAMICS

(71) Applicant: International Business Machines Corporation, Armonk, NY (US)

(72) Inventors: James R. Kozloski, New Fairfield, CT (US); Sara Berger, White Plains, NY (US); Anup Kalia, Elmsford, NY (US); Jeffrey L. Rogers, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 830 days.

(21) Appl. No.: 15/986,564

(22) Filed: May 22, 2018

(65) Prior Publication Data

US 2019/0362849 A1 Nov. 28, 2019

(51) Int. Cl.
*G06N 20/00* (2019.01)
*G16H 50/30* (2018.01)
*G06N 5/04* (2006.01)

(52) U.S. Cl.
CPC .............. *G16H 50/30* (2018.01); *G06N 5/04* (2013.01); *G06N 20/00* (2019.01)

(58) Field of Classification Search
CPC ........ G06N 20/00; G06N 20/10; G06N 20/20; G06N 5/04; G06N 5/022; G06N 5/003;

(Continued)

(56) References Cited

U.S. PATENT DOCUMENTS 5,908,383 A 6/1999 Brynjestad
6,249,809 B1 * 6/2001 Bro .................. H04M 3/493
709/217

(Continued)

FOREIGN PATENT DOCUMENTS

CN 102314558 A 1/2012
CN 105844112 A 8/2016

OTHER PUBLICATIONS

Non-Final Office Action received for U.S. Appl. No. 15/986,409 dated Jun. 25, 2020, 38 pages.

(Continued)

*Primary Examiner* — Dave Misir
(74) *Attorney, Agent, or Firm* — Amin, Turocy & Watson, LLP

(57) ABSTRACT

Techniques regarding autonomously determining an entity's susceptibility towards one or more treatment services are provided. For example, one or more embodiments described herein can comprise a system, which can comprise a memory that can store computer executable components. The system can also comprise a processor, operably coupled to the memory, and that can execute the computer executable components stored in the memory. The computer executable components can comprise an assessment component that can determine a susceptibility disposition value that measures a susceptibility of an entity to a treatment service based on a trust disposition value. The trust disposition value can be determined based on a communication with the entity using machine learning technology.

18 Claims, 10 Drawing Sheets

(58) Field of Classification Search
CPC ........ G06N 3/08; G06N 99/005; G16H 50/20; G16H 50/30; G16H 20/10; G16H 20/40; G16H 20/70

See application file for complete search history.

(56) References Cited

U.S. PATENT DOCUMENTS

| | | |
|---|---|---|
| 7,229,430 B2 | 6/2007 | Hickle et al. |
| 7,463,927 B1 | 12/2008 | Chaouat |
| 7,957,809 B2 | 6/2011 | Bourget et al. |
| 8,046,241 B1 | 10/2011 | Dodson |
| 8,086,563 B2 | 12/2011 | Jung et al. |
| 8,380,314 B2 | 2/2013 | Panken et al. |
| 8,380,531 B2 | 2/2013 | Paty et al. |
| 8,469,713 B2 | 6/2013 | Kron et al. |
| 9,147,041 B2 | 9/2015 | Amarasingham et al. |
| 9,262,688 B1 | 2/2016 | Zadeh |
| 9,536,049 B2 | 1/2017 | Brown et al. |
| 9,636,273 B1 | 5/2017 | Harris |
| 9,782,122 B1 | 10/2017 | Pulliam et al. |
| 2001/0012913 A1 | 8/2001 | Iliff |
| 2002/0128866 A1 | 9/2002 | Goetzke et al. |
| 2003/0178031 A1 | 9/2003 | Du Pen et al. |
| 2004/0064709 A1 | 4/2004 | Heath |
| 2006/0293572 A1 | 12/2006 | Bulat |
| 2007/0271272 A1 | 11/2007 | McGuire et al. |
| 2008/0059241 A1 | 3/2008 | Zahlmann et al. |
| 2009/0157141 A1 | 6/2009 | Chiao et al. |
| 2010/0087795 A1 | 4/2010 | Krijnsen et al. |
| 2010/0153832 A1 | 6/2010 | Markus et al. |
| 2011/0035158 A1 | 2/2011 | Banos et al. |
| 2011/0054564 A1 | 3/2011 | Valencia |
| 2012/0078837 A1 | 3/2012 | Bagchi et al. |
| 2013/0173277 A1 | 7/2013 | Eller et al. |
| 2013/0244336 A1 | 9/2013 | Mayer et al. |
| 2014/0074454 A1 | 3/2014 | Brown et al. |
| 2014/0074509 A1 | 3/2014 | Amarasingham et al. |
| 2014/0275827 A1 | 9/2014 | Gill et al. |
| 2014/0276188 A1 | 9/2014 | Jardin |
| 2014/0316793 A1* | 10/2014 | Pruit ................... G06F 19/00 705/2 |
| 2015/0019241 A1* | 1/2015 | Bennett ............... G16H 50/20 705/2 |
| 2015/0193583 A1* | 7/2015 | McNair ............... G16H 50/20 705/2 |
| 2015/0199484 A1 | 7/2015 | Morris et al. |
| 2015/0254408 A1 | 9/2015 | Dadlani Mahtani et al. |
| 2015/0287330 A1 | 10/2015 | Kron et al. |
| 2016/0100790 A1 | 4/2016 | Cantu et al. |
| 2016/0117484 A1* | 4/2016 | Hanina ................ G16H 20/10 705/3 |
| 2016/0198996 A1 | 7/2016 | Dullen |
| 2016/0210424 A1 | 7/2016 | Di Battista |
| 2016/0213314 A1 | 7/2016 | Zuckerman-Stark et al. |
| 2016/0335412 A1 | 11/2016 | Tucker et al. |
| 2016/0339241 A1 | 11/2016 | Hargrove et al. |
| 2017/0004260 A1 | 1/2017 | Moturu et al. |
| 2017/0056642 A1 | 3/2017 | Moffitt et al. |
| 2017/0124269 A1* | 5/2017 | McNair ................ G16H 10/60 |
| 2018/0018966 A1* | 1/2018 | Leonard ............... G06Q 10/10 |
| 2018/0039763 A1* | 2/2018 | Tidor .................... G16H 10/20 |
| 2018/0278554 A1* | 9/2018 | Kassabgi .............. G16H 50/70 |
| 2018/0307678 A1* | 10/2018 | Anantaram ............ G06N 3/08 |
| 2019/0140986 A1 | 5/2019 | Anderson et al. |

OTHER PUBLICATIONS

Non-Final Office Action received for U.S. Appl. No. 15/986,579 dated Aug. 6, 2020, 36 pages.
Non-Final Office Action received for U.S. Appl. No. 15/986,566 dated Jul. 24, 2020, 33 pages.
Non-Final Office Action received for U.S. Appl. No. 15/986,598 dated Aug. 7, 2020, 36 pages.
Notice of Allowance received for U.S. Appl. No. 15/986,409 dated Jan. 7, 2021, 44 pages.
Baker, et al., Experience and knowledge of pain management in patients receiving outpatient cancer treatment: What do older adults really know about their cancer pain?, Pain Medicine, 2014, pp. 52-60, vol. 15. No. 1.
Hallenbeck, Pain and Intercultural Communication, Handbook of Pain and Palliative Care, Chapter 2, 2013, 24 Pages.
Pinto, et al., Patient-centred communication is associated with positive therapeutic alliance: a systematic review, Journal of Physiotherapy, 2012, pp. 77-87. vol. 58.
Anonymous, Method and System for Enhanced Medication Management System, Nov. 25, 2016, 5 Pages.
Kalia, et al., Güven: estimating trust from communications, Journal of Trust Management, 2016, 19 Pages, vol. 3, No. 1.
Anonymous, Methods & devices for managing and monitoring arthritis patients, IP.com No. IPCOM000247325D; Aug. 23, 2016, 7 pages.
Temple, Enrichment Strategies for Clinical Trials, CDER Enrichment Webinar, Mar. 25, 2013, 40 Pages.
Victor, et al., Trustworthiness as a Clinical Variable: The Problem of Trust in the Management of Chronic, Nonmalignant Pain, Pain Medicine, 2005, pp. 385-391, vol. 6, No. 5.
Buchman, et al., You Present like a Drug Addict: Patient and Clinician Perspectives on Trust and Trustworthiness in Chronic Pain Management, Pain Medicine, 2016, p. 1394-1406, vol. 17.
Castle, et al., Neural and behavioral bases of age differences in perceptions of trust, PNAS, Dec. 12, 2012, pp. 20848-20852, vol. 109, No. 51.
Baliki, et al, Brain Morphological Signatures for Chronic Pain, PLoS ONE, Oct. 13, 2011, 13 Pages, vol. 6, No. 10.
Eickhoff, et al., Functional Segregation of the Human Dorsomedial Prefrontal Cortex, Cerebral Cortex, Jan. 2016, pp. 304-321, vol. 26.
Hashmi, et al., Shape shifting pain: chronification of back pain shifts brain representation from nociceptive to emotional circuits, Brain A Journal of Neurology, Jun. 14, 2013, pp. 2751-2768, vol. 136.
Fett, et al., Social neuroscience in psychiatry: unravelling the neural mechanisms of social dysfunction, Psychological Medicine, Sep. 18, 2014, 21 Pages.
Tsukiura, et al., Insular and hippocampal contributions to remembering people with an impression of bad personality, SCAN, 2013, pp. 515-522, vol. 8.
Vachon-Presseau, et al., Corticolimbic anatomical characteristics predetermine risk for chronic pain, Brain A Journal of Neurology, 2016, pp. 1958-1970, vol. 139.
Getov, et al., Human brain structure predicts individual differences in preconscious evaluation of facial dominance and trustworthiness, SCAN, 2015, pp. 690-699, vol. 10.
Mansour, et al., Brain white matter structural properties predict transition to chronic pain, Pain, Oct. 2013, pp. 2160-2168, vol. 154, No. 10.
Baliki, et al., Corticostriatal functional connectivity predicts transition to chronic back pain, National Neuroscience, pp. 1117-1119, vol. 15, No. 8.
Sprengelmeyer, et al., The neuropsychology of first impressions: Evidence from Huntington's disease, Cortex, Dec. 10, 2016, 41 Pages.
Baliki, et al., Predicting value of pain and analgesia: nucleus accumbens response to noxious stimuli changes in the presence of chronic pain, Neuron, Apr. 15, 2010, pp. 149-160, vol. 66, No. 1.
Tetreault, et al., Brain Connectivity Predicts Placebo Response across Chronic Pain Clinical Trials, PLOS Biology, Oct. 27, 2016, vol. 14, No. 10.
Pecina, et al., Personality Trait Predictors of Placebo Analgesia and Neurobiological Correlates, Neuropsychopharmacology, 2013, pp. 639-646, vol. 38.
Schafer, et al., Health Care Providers' Judgments in Chronic Pan: The Influence of Gender and Trustworthiness, International Association for the Study of Pain, 2016, 32 Pages.
Colloca, et al., Placebo analgesia induced by social observational learning, Pain, Jan. 29, 2009, pp. 28-34, vol. 144.

(56) References Cited

OTHER PUBLICATIONS

Geers, et al., Reconsidering the role of personality in placebo effects: Dispositional optimism, situational expectations, and the placebo response, Journal of Psychosomatic Research, 2005, pp. 121-127, vol. 58.
Hyland, et al., Motivational concordance: An important mechanism in self-help therapeutic rituals involving inert (placebo) substances, Journal of Psychosomatic Research, 2008, pp. 405-413, vol. 65.
Tuttle, et al., Increasing placebo responses over time in U.S. clinical trials of neuropathic pain, Pain, Dec. 2015, pp. 2616-2626, vol. 156.
Lount, The Impact of Positive Mood on Trust in Interpersonal and Intergroup Interactions, Journal of Personality and Social Psychology, 2010, pp. 420-433, vol. 98, No. 3.
Sessa, et al., Perceived trustworthiness shapes neural empathic responses toward others' pain, Neuropsychologia, 2015, pp. 97-105, vol. 79.
Mel, et al., The NIST Definition of Cloud Computing, National Institute of Standards and Technology Special Publication 800-145, Sep. 2011, 7 Pages.
Mutso et al., "Reorganization of hippocampal functional connectivity with transition to chronic back pain," Journal of Neurophysiology, 2014, pp. 1065-1076, 12 pages.
Final Office Action received for U.S. Appl. No. 15/986,409 dated Oct. 2, 2020, 44 pages.
Notice of Allowance received for U.S. Appl. No. 15/986,566 dated Nov. 3, 2020, 25 Pages.
List of IBM Patents or Applications Treated as Related.

\* cited by examiner

ASSESSING A TREATMENT SERVICE BASED ON A MEASURE OF TRUST DYNAMICS

PARTIES TO A JOINT RESEARCH AGREEMENT

The present subject matter was developed and the claimed invention was made by or on behalf of Boston Scientific Neuromodulation Corporation and International Business Machines Corporation, parties to a joint research agreement that was in effect on or before the effective filing date of the claimed invention, and the claimed invention was made as a result of activities undertaken within the scope of the joint research agreement.

BACKGROUND

The subject disclosure relates to assessing an individual's susceptibility to one or more treatment services, and more specifically, to autonomously determining an individual's susceptibility to one or more treatment services based on one or more trust dynamics measured using artificial intelligence technology.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses and/or computer program products that can autonomously assess an entity's susceptibility to one or more treatment services based on a trust dynamic measured using artificial intelligence technology are described.

According to an embodiment, a system is provided. The system can comprise a memory that can store computer executable components. The system can also comprise a processor, operably coupled to the memory, and that can execute the computer executable components stored in the memory. The computer executable components can comprise an assessment component that can determine a susceptibility disposition value that measures a susceptibility of an entity to a treatment service based on a trust disposition value. The trust disposition value can be determined based on a communication with the entity using machine learning technology.

According to an embodiment, a computer-implemented method is provided. The computer-implemented method can comprise determining, by a system operatively coupled to a processor, a susceptibility disposition value that measures a susceptibility of an entity to a treatment service based on a trust disposition value. The trust disposition value can be determined based on a communication with the entity using machine learning technology.

According to an embodiment, a computer program product for autonomously assessing a treatment service is provided. The computer program product can comprise a computer readable storage medium having program instructions embodied therewith. The program instructions can be executable by a processor to cause the processor to determine, by a system operatively coupled to the processor, a susceptibility disposition value that measures a susceptibility of an entity to a treatment service based on a trust disposition value. The trust disposition value can be determined based on a communication with the entity using machine learning technology.

DETAILED DESCRIPTION

Figure 1:
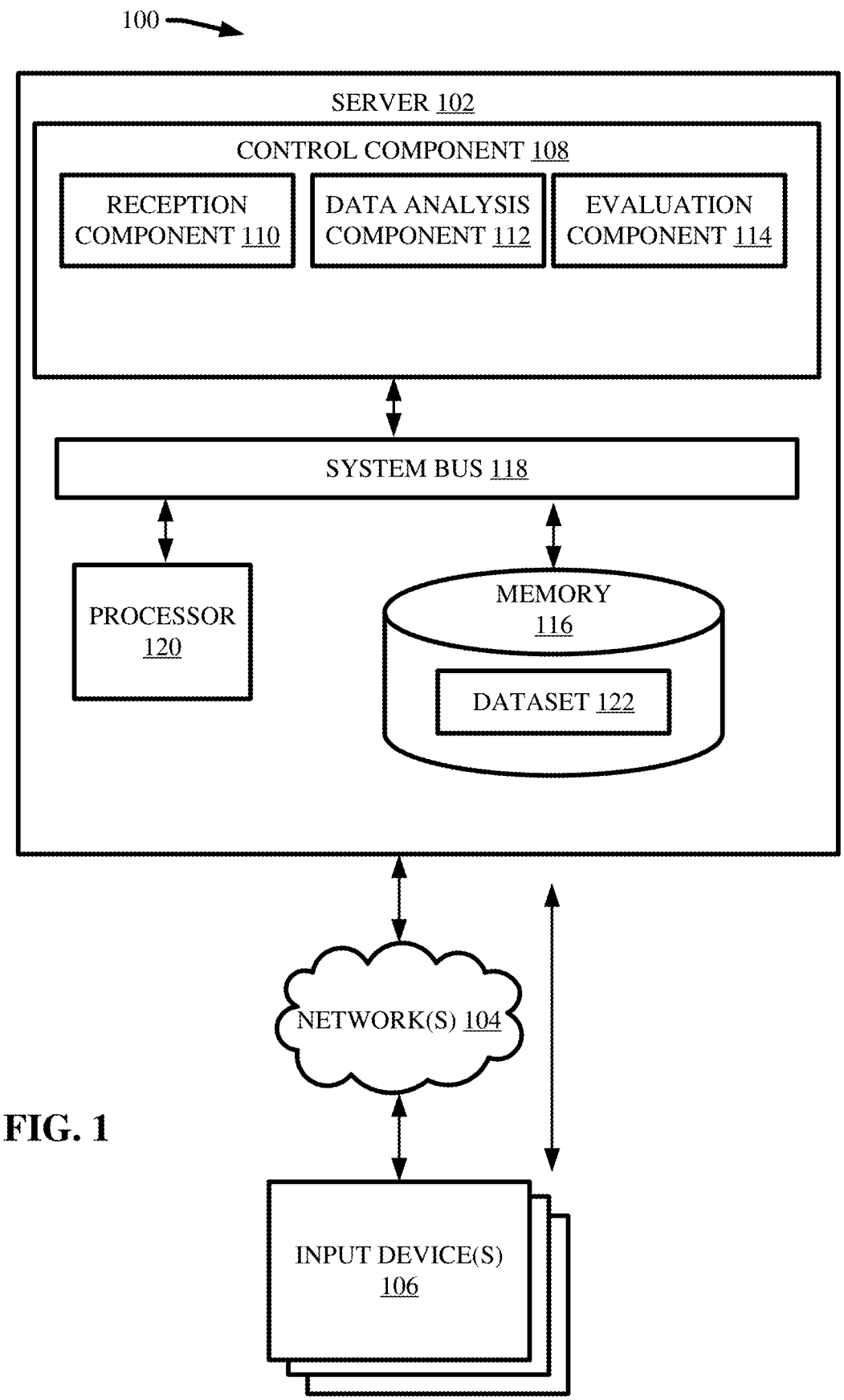
FIG. 1 illustrates a block diagram of an example, non-limiting system that can determine a trust disposition value regarding an entity in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Medicines can exhibit side-effects and/or can cause adverse health conditions to patients consuming the medicine. For example, some medicines can induce a chemical dependency within the patient, wherein the patient experiences a chemical reaction caused by the medicine that encourages the patient to consume more of the medicine. In some instances, the side-effects (e.g., induced chemical dependency) can result in the patient using the medicine via methods, dosages, and/or frequency not authorized by a medical professional. In such instances, treatment services exist to assist the patient in inhibiting the side-effect (e.g., inhibit the chemical dependency and thereby the improper consumption of medicine). However, conventional techniques seek to distribute the treatment services in response to identifying that the patient is suffering from a side-effect without regard as to whether the patient is likely to be susceptible to the treatment services (e.g., as determined through a measurable metric).

Various embodiments of the present invention can be directed to computer processing systems, computer-implemented methods, apparatus and/or computer program products that facilitate the efficient, effective, and autonomous (e.g., without direct human guidance) determining an entity's expected susceptibility to one or more treatment services using artificial intelligence ("AI") technology. For instance, one or more embodiments described herein can exploit a relationship between an entity's trust and an effectiveness of a treatment service regarding the entity, thereby providing a window into the entity's likely responsiveness to the one or more treatment services. Therefore, one or more embodiments can use a relationship between a treatment service's effectiveness and trust dynamics of the entity (e.g., the patient) to autonomously determine the entity's expected susceptibility disposition towards the treatment service and/or distribute the treatment service based on the expected susceptibility disposition.

For example, in one or more embodiments described herein can regard measuring, via one or more AI technologies, a trust dynamic associated with an entity (e.g., a patient) and/or can determine the entity's expected susceptibility disposition values towards one or more treatment services based on the measured trust dynamic. Measuring the trust dynamic can be achieved by analyzing one or more electronic communications, wherein commitments regarding the entity can be identified and found to be fulfilled and/or unfulfilled. The trust dynamic can be indicative of the entity's responsiveness to a medicine and/or a treatment service. Further, various embodiments can autonomously distribute one or more treatment services based on one or more expected susceptibility disposition values regarding the one or more treatment services.

The computer processing systems, computer-implemented methods, apparatus and/or computer program products employ hardware and/or software to solve problems that are highly technical in nature (e.g., determining an entity's expected susceptibility towards one or more treatment services based on one or more analytically computed trust disposition values that can characterize one or more trust dynamics associated with an entity), that are not abstract and cannot be performed as a set of mental acts by a human. For example, an individual, or even a plurality of individuals, cannot readily collect, maintain, and/or analyze vast volumes of data as expeditiously and/or efficiently as the various embodiments described herein. Additionally, one or more embodiments described herein can utilize AI technologies that are autonomous in their nature to facilitate determinations and/or predictions that cannot be readily performed by a human.

Within a patient's brain, correlations can be found between various ailments affecting the patient and one or more trust dynamics. For example, a correlation can exist between chronic pain and a patient's disposition to trust (e.g., in a medical professional and/or in a medicine). As used herein, the term "pain" can refer to an unpleasant sensory and/or emotional experience associated with actual or potential tissue damage. Also, as used herein, the term "chronic pain" can refer to pain that persists past a healing period, having widespread effects that can influence one or more levels of a nervous system. Chronic pain can persist for greater than or equal to three months and/or can significantly impact a person's psychological well-being.

In 2010, the American Academy of Pain Medicine ("AAPM") estimated that over 100 million Americans suffer from a chronic pain condition, and said conditions can cos the United States over 500 billion dollars annually from health care costs and/or lost productivity. Diagnosing and/or treating chronic pain conditions can be difficult clinical tasks and/or can be further complicated by patient-physician dynamics, such as trust preservation over the course of the client-practitioner relationship.

Chronic pain and trust, while being distinct experiences, can have considerable overlap physiologically and/or psychologically. For example, from a neuroscience perspective, both phenomena can rely on some of the same brain regions and/or similar brain networks involved in emotional processing, emotional regulation, interoceptive awareness, memory consolidation, memory recall, decision making, and/or social attribution learning. The subject brain portions can include, for example: the insula, the anterior cingulate cortex ("ACC"), the posterior cingulate cortex, the hippocampus, the amygdala, and/or the frontal cortices (e.g., the medial prefrontal cortex ("mPFC")). Evidence of the shared neurocircuitry between aliments (e.g., chronic pain) and trust can be found both at a structural level (e.g., by analyzing grey and/or white mater properties within a patient's brain) and/or at a neurophysiological level (e.g., by analyzing functional connects between brain regions while a patient is at rest and/or performing a task). Due at least to the described correlations, a patient's level of trust can interact and/or influence their ailment (e.g., chronic pain), including responsiveness to a treatment regarding the ailment.

Furthermore, ailments, such as pain, and trust can have aspects of trait-like and/or state-like qualities, which can be considered when analyzing trust dynamics of a patient. Regarding trait-like qualities, a patient's brain structure (e.g., grey matter density, volume, the shape of subcortical regions, and/or the number of white matter connections) can facilitate predicting the patient's likelihood of developing an ailment (e.g., chronic pain). Also, functional connectivity between nucleus accumbens and/or the mPFC can facilitate predicting one or more transitions between states of the ailment (e.g., a transition from acute pain to chronic pain). Thus, a patient's brain structure can predispose the patient to a have an increased likelihood of suffering from the ailment (e.g., chronic pain), even before a triggering event (e.g., an injury).

Similarly, a patient's brain structure can also facilitate in predicting individual differences in preconscious evaluation of another's trustworthiness (e.g., gray matter volume of the mPFC can be correlated to a perceived untrustingness of others). For example, diffusion-tensor imaging ("DTI") can show differences in functional anisotropy ("FA") measures of white matter tract integrity around brain regions involved in social cognition between individuals with normal vs impaired perceptions of trustworthiness. Since structural properties of gray matter and white matter do not change drastically in short time frames, such imaging suggest that individuals may be predisposed in the extent to which they can trust a person and/or situation.

Regarding state-like qualities, both trust and one or more ailments (e.g., chronic pain) can be non-stationary over time (e.g., due to a patient's life experiences in combination with their underlying neuropsychological pre-dispositions). Also, the strength of functional connectivity between the dorsomedial prefrontal cortex ("dmPFC") and the ACC and/or between the insula and the hippocampus can change as a function of perceived trustworthiness. Further, empathy towards another's ailment (e.g., pain) can be shaped by perceived trustworthiness and reflected in modulated neural processing with reduced activations of emotional processing regions when observing someone less trustworthy. Trust can also be affected by the patient's current emotional state and/or mood. Similarly, some aliments (e.g., pain) can have dynamic properties such as: varying durations, varying intensities, and/or varying perceived locations. For example, long lasting ailments (e.g., chronic pain) can fluctuate about a mean intensity and/or exhibit peaks in intensity due to external triggers. For instance, neuroimaging can show that dynamics in subjective pain ratings can be reflected in the functional connectivity of sensory and/or emotional brain networks. Also, neurophysiological activity can change as a function of the intensity of pain and/or effectiveness of a medication, even a placebo. Further, like trust, a patient's mood can impact the severity of an ailment (e.g., severity of pain) perceived by a patient. Thus, in addition to predisposing factors, one or more ailments (e.g., pain) and trust can both produce dynamics that can be tracked in time and linked to internal and/or external perturbations. Moreover, one or more ailments (e.g., chronic pain) and trust can share temporal, affective, and/or social contexts. For example, both phenomena can increase with age (e.g., older individuals can be more likely to suffer from chronic pain and can be more trusting).

Thus, trust can play a significant role in any successful therapeutic interaction and/or relationship. For example, in the case of chronic pain management, the ability to trust can influence the effectiveness of pain relief medications. Factors potentially involved in trust dynamics between a patient and a physician can span previous experiences, current contexts, and/or expected future occurrences. Example factors that can influence a physician's trust for a patient can include, but are not limited to: the patient's subjective report and/or overall demeanor, the patient's potential motives to seek treatment, the patient's potential level of responsibility, previous experience with patients suffering from the same ailment, discussions with colleagues who may or may not have referred the patient, and/or medical culture at the time. Example factors that can influence a patient's trust for a physician can include, but are not limited to: the physician's interpersonal interaction with the patient, the physician's reputation, whether the physician's prescribed advice and/or therapy makes the patient feel better, previous experience with other physicians, previous experience with similar treatments for the ailment, previous experience with different treatment for the ailment.

The claims and scope of the subject application, and any continuation, divisional or continuation-in-part applications claiming priority to the subject application, exclude embodiments (e.g., systems, apparatus, methodologies, computer program products and computer readable storage media) directed to implanted electrical stimulation for pain treatment and/or management.

FIG. 1 illustrates a block diagram of an example, non-limiting system 100 that can determine one or more entities' susceptibility towards one or more treatment services based on a determined trust disposition value in accordance with one or more embodiments described herein. Aspects of systems (e.g., system 100 and the like), apparatuses or processes in various embodiments of the present invention can constitute one or more machine-executable components embodied within one or more machines, e.g., embodied in one or more computer readable mediums (or media) associated with one or more machines. Such components, when executed by the one or more machines, e.g., computers, computing devices, virtual machines, etc. can cause the machines to perform the operations described.

As shown in FIG. 1, the system 100 can comprise one or more servers 102, one or more networks 104, and/or one or more input devices 106. The server 102 can comprise control component 108. The control component 108 can further comprise reception component 110, data analysis component 112, and/or evaluation component 114. Also, the server 102 can comprise or otherwise be associated with at least one memory 116. The server 102 can further comprise a system bus 118 that can couple to various components such as, but not limited to, the control component 108 and associated components, memory 116 and/or a processor 120. While a server 102 is illustrated in FIG. 1, in other embodiments, multiple devices of various types can be associated with or comprise the features shown in FIG. 1. Further, the server 102 can communicate with a cloud computing environment via the one or more networks 104.

The one or more networks 104 can comprise wired and wireless networks, including, but not limited to, a cellular network, a wide area network (WAN) (e.g., the Internet) or a local area network (LAN). For example, the server 102 can communicate with the one or more input devices 106 (and vice versa) using virtually any desired wired or wireless technology including for example, but not limited to: cellular, WAN, wireless fidelity (Wi-Fi), Wi-Max, WLAN, Bluetooth technology, a combination thereof, and/or the like. Further, although in the embodiment shown the control component 108 can be provided on the one or more servers 102, it should be appreciated that the architecture of system 100 is not so limited. For example, the control component 108, or one or more components of control component 108, can be located at another computer device, such as another server device, a client device, etc.

The one or more input devices 106 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. A user of the system 100 can utilize the one or more input devices 106 to input data into the system 100, thereby sharing (e.g., via a direct connection and/or via the one or more networks 104) said data with the server 102. For example, the one or more input devices 106 can send data to the reception component 110 (e.g., via a direct connection and/or via the one or more networks 104). Additionally, the one or more input devices 106 can comprise one or more displays that can present one or more outputs generated by the system 100 to a user. For example, the one or more displays can include, but are not limited to:

cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

In one or more embodiments, the control component 108 can analyze data (e.g., including data entered into the system 100 via the one or more input devices 106) to determine a trust disposition value using one or more machine learning technologies. As used herein, the term "machine learning technologies" can refer to an application of AI technologies to automatically learn and/or improve from an experience (e.g., training data) without explicit programming of the lesson learned and/or improved. Also, as used herein, the term "trust disposition value" can refer to a numerical value that can represent an entity's current likeliness to trust another individual, medicine, medical treatment, therapy, and/or situation.

Typical approaches in defining and/or estimating trust can be classified as conceptual approaches and/or computational approaches. Conceptual approaches can consider the intuitive aspects of trust. For example, a person providing the trust ("a trustor") can be vulnerable to decisions made by a person receiving said trust ("a trustee"). However, conceptual approaches lack a means to compute a trust disposition value that can represent said intuitive aspects of trust. Conventional computational approaches can compute a trust value, but are domain-specific and emphasize numerical heuristics, thereby ignoring the intuitiveness behind trust. In one or more embodiments, the control component 108 can bridge the gap between the typical conceptual and computational approaches by determining a trust disposition value based on one or more commitments. For example, the one or more commitments can be represented as "C(debtor, creditor, antecedent, consequent)," wherein the debtor can commit to bring about the consequent for the creditor provided the antecedent holds. For instance "C(physician, patient, visiting the physician, providing a medical report)" can be an exemplary commitment, wherein: the physician can be debtor, the patient can be the creditor, the antecedent can be visiting the physician, and/or the consequent can be providing a medical report. When the physician provides the medical report, the example commitment is satisfied. If the physician fails to provide the medical report, the example commitment is violated. Thus, one or more commitments can, for example, capture social relationships between a physician and a patient, thereby providing a basis for computing trust between the entities. Based at least on data regarding one or more commitments, the control component 108 can utilize machine learning technologies to determine one or more trust disposition values.

The reception component 110 can receive the data entered by a user of the system 100 via the one or more input devices 106. The reception component 110 can be operatively coupled to the one or more input devices 106 directly (e.g., via an electrical connection) or indirectly (e.g., via the one or more networks 104). Additionally, the reception component 110 can be operatively coupled to one or more components of the server 102 (e.g., one or more component associated with the control component 108, system bus 118, processor 120, and/or memory 116) directly (e.g., via an electrical connection) or indirectly (e.g., via the one or more networks 104).

In various embodiments, the reception component 110 can utilize one or more AI technologies to identify and/or request data from an entity (e.g., a patient). For example, the reception component 110 can use one or more chatbots (e.g., a talkbot, a chatterbot, a chatterbox, and/or an artificial conversational entity) to facilitate one or more communications between the entity and the reception component 110 (e.g., via the one or more input devices 106 and/or the one or more networks 104). The one or more communications can regard one or more commitments involving the subject entity (e.g., patient). As used herein, the term "chatbot" can refer to a computer program that can conduct one or more conversations with an entity (e.g., a patient) via auditory and/or textual methods. The one or more chatbots can be designed to convincingly simulate how a human could converse, thereby passing the Turing test.

The one or more chatbots can use a sophisticated natural language processing system (e.g., such as IBM WATSON®, other purveyors of pre-build intents and/or dialogue flows, and/or like) and/or can scan for keywords within an input (e.g., entered via the one or more input devices 106) and pull a stored reply comprising the most matching keywords and/or most similar wording patterning from a database. For example, the one or more chatbots can function based on one or more rules. In another example, the one or more chatbots can use AI technology to understand language and/or continually learn from conversations.

One or more entities can use the one or more input devices 106 to interact with the reception component 110 (e.g., via the one or more networks 104) and provide data to the control component 108. The received data can regard one or more communications regarding a subject entity (e.g., a patient) and/or can be stored in one or more datasets 122. The one or more datasets 122 can be located in the memory 116 and/or in another location in a cloud computing environment (e.g., accessible via the one or more networks 104). For example, the one or more chatbots can inquire into one or more commitments involving the entity (e.g., the patient). For instance, the one or more chatbots can communicate regarding, for example: past experiences with a physician; past experiences with a subject medicine; past experiences with a treatment; expectations regarding a physician, medication, and/or treatment; a level of satisfaction with a subject physician, medication and/or treatment; and/or a perceived reputation of a subject physician, medication and/or treatment.

The data analysis component 112 can extract one or more features from the one or more datasets 122 and/or from one or more external sources (e.g., via the one or more networks 104). The extracted features can represent, for example, the debtor, the creditor, the antecedent, and/or the consequent of a subject commitment. In other words, the data analysis component 112 can analyze the data received and/or stored by the reception component 110 (e.g., via one or more chatbots) and extract one or more features that can represent one or more commitments involving the subject entity (e.g., subject patient).

Further, in one or more embodiments the data analysis component 112 can analyze data (e.g., electronic communications) regarding the entity from one or more external sources (e.g., data not entered via an engagement with the reception component 110). For example, a subject entity (e.g., a subject patient) can grant the data analysis component 112 access to one or more emails involving the entity. The data analysis component 112 can analyze the one or more emails to identify one or more commitments and/or extract one or more features regarding the one or more commitments.

The data analysis component 112 can use natural language processing to extract the one or more features, wherein the one or more features can be ngrams (e.g., unigrams and/or bigrams), modal verbs, action verbs, and/or deadline from one or more sentences of the conversations regarding the subject entity (e.g., via interaction with one or more chatbots and/or via communication with another individual, such as by email). Subsequently, the data analysis component 112 can train a classifier program (e.g., such as a support vector machine, a deep neural network, a random forest and/or decision forest, and/or like) based on the one or more extracted features.

In various embodiments, the evaluation component 114 can determine one or more commitment operations based on the one or more extracted features and/or generate one or more trust disposition values. The evaluation component 114 can represent trust as binary evidence "<r,s>;" wherein "r" can represent a positive experience involving the entity and can be greater than or equal to zero, and wherein "s" can represent a negative experience involving the entity and can be greater than or equal to zero. Thus, one or trust disposition values can be computed by the evaluation component 114 as the probability of a positive outcome, which can be represented by "α" as shown in Equation 1 below.

$$\alpha = \frac{r}{r+s} \quad \text{Equation 1}$$

The control component 108 (e.g., via the reception component 110, the data analysis component 112, and/or the evaluation component 114) can maintain evidence "<r,s>" about a subject entity (e.g., a patient), wherein an initial evidence, "<$r_{in}$, $s_{in}$>" can represent the entity's bias. One or more interactions between the entity and a physician, medicine, and/or medical treatment (e.g., as characterized by one or more commitments represented via one or more communications) can yield a positive, negative, or neutral experience. Thus, with each interaction (e.g., with each communication captured by the one or more chatbots and/or an external source such as email) the entity's initial evidence can be updated by adding "<$i_r$,0>", "<0,$i_s$>" and "<$\lambda i_r$, $(1-\lambda)i_s$>"; wherein $\lambda \in [0,1]$, wherein "$i_r$" can represent new evidence of a positive experience, and wherein "$i_s$" can represent new evidence of a negative experience. Therefore, the evaluation component 114 can determine an entity's trust disposition value based on at least the five parameters: "$i_r$", "$i_s$", "$r_{in}$", "$s_{in}$", and/or "$\lambda$." To learn the parameters based on positive experiences (e.g., represented by "$E^+$"), negative experiences (e.g., represented by "$E^-$"), and/or neutral experiences (e.g., represented by "E"), the evaluation component 114 can represent the trust disposition value in accordance with Equation 2 below.

$$\alpha = \frac{r_{in} + (i_r * E^+) + \lambda * i_r * E}{r_{in} + s_{in} + (i_r * E^+) + (i_s * E^-) + E(\lambda * i_r + (1-\lambda)i_s)} \quad \text{Equation 2}$$

For example, Table 1, provided below, can depict exemplary analysis (e.g., via the data analysis component 112) and/or evaluation (e.g., via evaluation component 114) of multiple email interactions (e.g., communications involving one or more commitments) involving an entity. As shown in Table 1, commitment operations can be determined based on one or more features extracted from the emails. The commitment operations can delineate, for example, that: a commitment has been created (e.g., represented by "create($C_1$)," which can indicate that a first commitment has been created, and/or by "create($C_2$)," which can indicate that a second commitment has been created); that a commitment has been fulfilled (e.g., represented by "satisfied ($C_1$);" and/or that a commitment has been violated (e.g., represented by "violate ($C_2$)."

TABLE 1

| Sender | Receiver | Email | Operation |
|---|---|---|---|
| Kim | Dorothy | I will check with Alliance Travel Agency . . . | create($C_1$) |
| Kim | Dorothy | I checked with our Travel Agency . . . | satisfied($C_1$) |
| Rob | Kim | By Wednesday, please send all copies of your documentation . . . | create($C_2$) |
| Kim | Rob | Rob, please forgive me for not sending . . . | violate($C_2$) |

Additionally, Table 2, presented below, can depict computed trust disposition values that can represent relationships of trust characterized by the exemplary email interactions depicted in Table 1. As shown in Table 1, there are two exemplary email interactions between Kim and Dorothy. As shown in Table 2, amongst the two said email interactions, Kim's trust in Dorothy remains neutral (e.g., represented by "E=2") at least because Dorothy has neither fulfilled a commitment (e.g., represented by "$E^+$=0") nor violated a commitment (e.g., represented by "$E^-$=0"). Also, as shown in Table 2, amongst the two email interactions between Kim and Dorothy, Dorothy's trust in Kim is positive at least because: the first email interaction created a commitment, and was thus neutral (e.g., represented by "E=1"), and the second email interaction fulfilled a commitment (e.g., represented by "$E^+$=1") without violating a commitment between the entities (e.g., represented by "$E^-$=0"). Further, as shown in Table 2: "S1-S5" can represent possible trust disposition values created by analyzing the communications and/or interactions between Kim and Dorothy.

TABLE 2

| Trust Pairs | Experiences | S1 | S2 | S3 | S4 | S5 |
|---|---|---|---|---|---|---|
| Kim → Dorothy | E = 2, $E^+$ = 0, $E^-$ = 0 | 0.45 | 0.6 | 0.8 | 0.6 | 0.56 |
| Dorothy → Kim | E = 1, $E^+$ = 1, $E^-$ = 0 | 0.7 | 0.9 | 0.8 | 0.76 | 0.84 |

One of ordinary skill in the art will recognize that while the exemplary data depicted in Table 1 and/or Table 2 can be derived from an external source (e.g., one or more email accounts), data analyzed and/or evaluated by the control component 108 (e.g., via the data analysis component 112 and/or the evaluation component 114) can be received through one or more communications with a subject entity by AI technology (e.g., one or more chatbots utilized by the reception component 110). Furthermore, while the exemplary data depicted in Table 1 and/or Table 2 depicts one or more trust relations (e.g., characterized by one or more trust disposition values) between two individuals (e.g., a patient/physician relationship), one or more trust disposition values can also characterize trust relations between an entity and an object (e.g., a medicine) and/or an event (e.g., medical treatment and/or therapy). For example, data received by the reception component 110 (e.g., via one or more chatbots) and/or analyzed by the data analysis component 112 can regard an entity's past experiences and/or future expectations regarding a medicine and/or medical treatment. For instance, one or more commitments comprised with the one or more communications can regard fulfillment and/or violation of results expected to be achieved by a medicine and/or medical treatment.

Thus, in various embodiments the control component 108 (e.g., via the reception component 110) can receive data representing one or more communications involving an entity (e.g., a patient). The received data can regard one or more commitments that can influence the entities disposition to provide trust. The control component 108 can determine one or more initial trust values (e.g., an initial trust disposition value) based on the data. Also, the control component 108 can extract one or more features from the data to train machine learning technologies, which can update the initial trust value to represent trust predictions that can characterize future trust relations involving the entity (e.g., updated trust disposition values). Thus, the control component 108 can determine a trust disposition value regarding one or more relationships involving an entity (e.g., a patient) and/or can update the trust disposition value as new data (e.g., communications involving the entity) is received (e.g., via the reception component 110 and/or an external source such as email correspondences). Furthermore, in one or more embodiments the control component 108 can maintain the currency of one or more of the trust disposition values by updating said trust disposition values based on the periodic collection of new data. For example, the reception component 110 can receive new data (e.g., via the one or more chatbots) and/or the data analysis component 112 can analyze new data at predefined periodic intervals (e.g., each day, each week, each month, and/or the like). Further the evaluation component 114 can update one or more trust disposition values based on the most recent data and/or data analysis (e.g., most recent extract features). In other words, the functions of the control component 108 can be repeated periodically to ensure the trust disposition values are up-to-date and accurately represent the current disposition of an entity.

Figure 2:
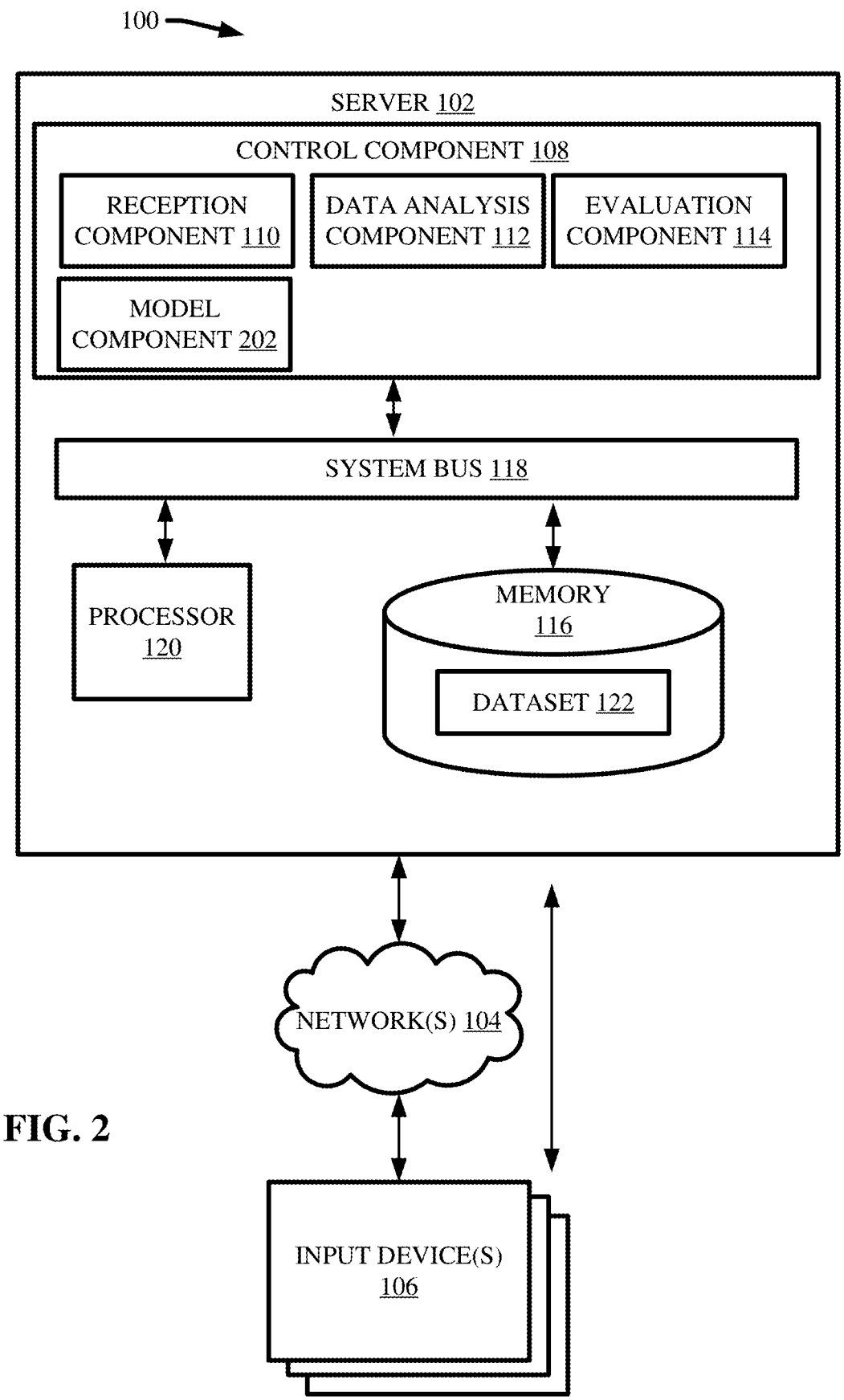
FIG. 2 illustrates a block diagram of an example, non-limiting system that can determine a trust disposition value regarding an entity in accordance with one or more embodiments described herein.

FIG. 2 illustrates a block diagram of the example, non-limiting system 100 further comprising model component 202 in accordance with one or more embodiments described herein. Repetitive description of like elements employed in other embodiments described herein is omitted for sake of brevity.

The model component 202 can generate one or more trust graphs, which can facilitate determining trust disposition values regarding a new relationship involving the entity based on one or more trust disposition values regarding other relationships involving the entity. As used herein, the term "trust graph" can refer to a computer model that depicts linkages between individuals and/or objects (e.g., medicines and/or medical treatments) through which trust can be represented (e.g., via one or more trust disposition values) and/or traversed algorithmically. For example, one or more linkages of a trust graph can depict how a subject entity (e.g., a patient) can be indirectly correlated to a target individual and/or object through one or more intermediate individuals and/or objects. Further, trust disposition values associated with the subject entity and the one or more intermediate individuals and/or object can facilitate predicting a trust disposition value associated with an indirect relationship between the subject entity and the target individual and/or object, despite a lack of previous experience and/or communication between the subject entity and/or the target individual and/or object.

For instance, one or more trust graphs generated by the model component 202 can depict a direct linkage between Fred and Fred's friend Harry. Further, the one or more trust graphs can depict a high trust disposition value associated with the direct link between Fred and Harry, thereby indicating, for example, that Fred has a high disposition of trust towards Harry. Also, the one or more trust graphs can depict a direct linkage between Harry and Harry's doctor, Dr. Lou. Further, the one or more trust graphs can depict a high trust disposition value associated with the direct link between Harry and Dr. Lou, thereby indicating, for example, that Harry has a high disposition of trust towards Dr. Lou. Harry can refer Fred to Dr. Lou, wherein a trust disposition value regarding Fred's disposition of trust towards Dr. Lou can be predicted at least because Harry can act as an intermediary to establish an indirect linkage between Fred and Dr. Lou. Thus, the model component 202, via the one or more trust graphs, can predict that Fred has a high disposition of trust towards Dr. Lou despite no previous encounters between the two individuals based on the high disposition values associated with the direct linkages (e.g., the direct link between Fred and Harry and/or the direct link between Harry and Dr. Lou) that form the indirect link between Fred and Dr. Lou.

Thus, in various embodiments the model component 202 can predict one or more disposition values associated with one or more new relationships based on one or more disposition values associated with established relationships that have influenced the one or more new relationships. Wherein a subject relationship (e.g., between a patient and a physician, between a patient and a medicine, and/or between a patient and a medical treatment) is established through one or more intermediary relationships, a trust disposition value characterizing the subject relationship can be predicted (e.g., via the model component 202) based on one or more trust disposition values associated with the one or more intermediary relationships. In other words, the model component 202 can predict one or more trust disposition values associated with an indirect relationship (e.g., a relationship that can lack previous interaction between subject entities) based on one or more trust disposition values associated with one or more direct relationships (e.g., a relationship that can be characterized by past interactions, such as commitments, between the subject entities).

Figure 3:
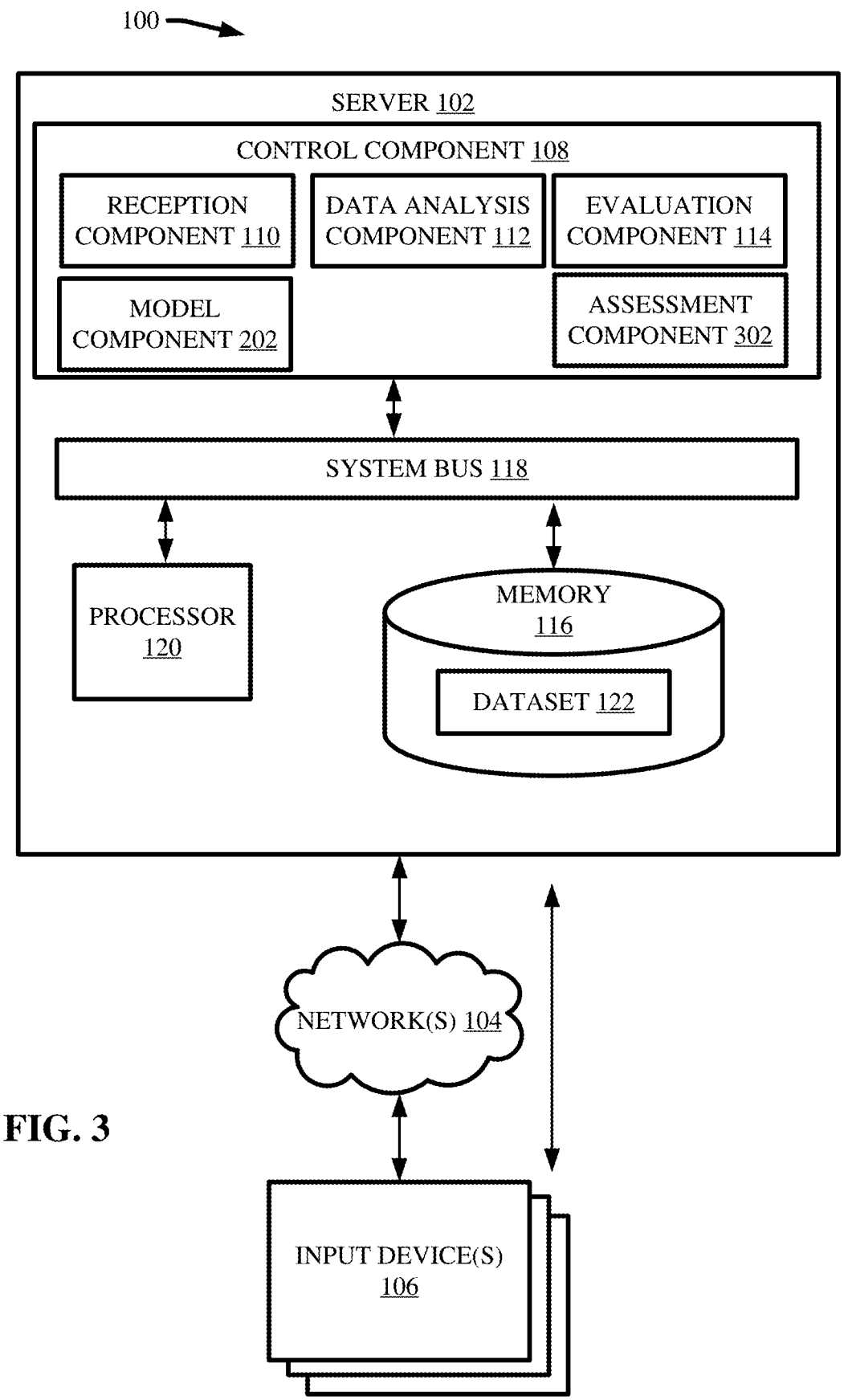
FIG. 3 illustrates a block diagram of an example, non-limiting system that can determine the susceptibility of one or more entities towards one or more treatment services based on at least a trust disposition value regarding the one or more entities in accordance with one or more embodiments described herein.

FIG. 3 illustrates a block diagram of the example, non-limiting system 100 further comprising assessment component 302 in accordance with one or more embodiments described herein. Repetitive description of like elements employed in other embodiments described herein is omitted for sake of brevity.

In various embodiments, the assessment component 302 can determine one or more susceptibility disposition values regarding an entity's expected susceptibility towards one or more treatment services based on one or more determined and/or predicted trust disposition values. As used herein, the term "treatment service" can refer to one or more services designed to treat and/or inhibit side-effects and/or adverse health conditions (e.g., brain disease) afflicting an entity (e.g., a patient) as a result of consumption of a chemical compound (e.g., a medicine). An example side-effect and/or adverse health condition can be a chemical dependency induced by a chemical compound (e.g., a medicine), wherein a patient consuming the medicine is encouraged, via the experience of a chemical reaction, to consume more of the chemical compound (e.g., via unrecommended methods, dosages, and/or frequency). Treatment services can engage an entity via visual, textural, and/or audible means. For example, treatment services can be presented via a video, a pamphlet, a book, a recording, a message (e.g., an email service and/or a text service), a counseling session (e.g., with a therapist and/or a phycologist), a webinar, a phone call, a combination thereof, and/or the like. Additionally, example treatment services can include, but are not limited to, enhanced monitoring of side-effects and/or adverse health conditions afflicting an entity. Further, one or more treatment services (e.g., counseling sessions) can be facilitated by real and/or virtual hosts (e.g., virtual counselors). Moreover, treatment services can be offered to the entity and/or a close relation to the entity (e.g., a friend, family member, spouse, co-worker, and/or the like).

In one or more embodiments, the control component 108 (e.g., via the reception component 110, the data analysis component 112, and/or the evaluation component 114) can determine trust disposition values regarding one or more relationships associated with an entity. For example, an entity's trust in one or more medical professionals can be characterized by a first trust disposition value. The entity's trust in a chemical compound (e.g., a medicine) can be characterized by a second trust disposition value. The entity's trust in a side affect and/or adverse health condition associated with a chemical compound, such as medicine, (e.g., trust in the likelihood in said side-effect and/o adverse health condition occurring) can be characterized by a third trust disposition. Further, an entity's trust disposition towards individuals and/or events in general can be characterized by a fourth trust disposition value (e.g., an and/or cumulative average trust disposition value). Thus, one of ordinary skill in the art will recognize that an entity can be characterized by a plurality of trust disposition values and/or predicted trust disposition values (e.g., via one or more trust graphs) that can characterize various relationships between the entity and an individual and/or an object (e.g., a chemical compound, a side-effect, and/or a treatment service).

As discussed herein, an entity's (e.g., a patient) trust in an individual (e.g., a physician) and/or an object (e.g., a medicine and/or a medical treatment) can affect one or more responses the entity has regarding a service of the individual and/or object. For example, a patient's trust in his/her physician can influence the effectiveness of one or more treatment services prescribed, endorsed, and/or administered by the physician with regards to the patient. In another example, a patient's expected trust in one or more treatment services can influence the effectiveness of the one or more treatment services. Thus, the one or more trust disposition values determined by the control component 108 (e.g., via the data analysis component 112, the evaluation component 114, and/or the model component 202) can be indicative of an expected effectiveness of one or more medicines and/or treatment services.

For example, wherein an entity has a large amount of trust in a treatment service (e.g., due to one or more positive past experiences with the treatment service and/or one or more positive indirect relationships, such as recommendations, with the treatment service), the treatment service can demonstrate a high effectiveness in treating and/or inhibiting one or more side-effects and/or adverse health conditions resulting from a chemical compound (e.g., chemical dependency). In another example, wherein the entity has a low amount of trust in a treatment service (e.g., due to one or more negative past experiences with the treatment service and/or one or more negative indirect relationships, such as recommendations, with the treatment service), the treatment service can demonstrate a low effectiveness in treating and/or inhibiting one or more side-effects and/or adverse health conditions resulting from a chemical compound (e.g., chemical dependency).

In one or more embodiments, the assessment component 302 can compare and/or analyze one or more trust disposition values to determine one or more susceptibility disposition values. As used herein, the term "susceptibility disposition value" can refer to an entity's expected susceptibility towards one or more treatment services being effective in inhibiting and/or treating a side-effect and/or adverse health condition caused by a chemical compound (e.g., a medicine). For example, the susceptibility disposition values can be based on various factors including, but not limited to: a likelihood that the entity is suffering from a side-effect and/or adverse health condition caused by a chemical compound (e.g., a medicine); a likelihood an entity will be responsive to one or more treatment services; the entity's expected disposition towards the side-effect and/or adverse health condition; a combination thereof, and/or the like. Each factor can be characterized by one or more trust disposition values, individually and/or collectively. Additionally, one or more medical diagnoses (e.g., performed by a medical professional) can supplement characterization of the factors, alone or in conjunction with one or more trust disposition values.

For example, one or more trust disposition values can be indicative of one or more risk factors related to vulnerability of the entity to a subject side-effect and/or adverse health condition (e.g., chemical dependency). In another example, one or more trust disposition values can characterize relationships that can affect an expected responsiveness to one or more treatment services; including, for example, an entity's disposition of trust towards: a medical professional who recommends the one or more treatment services, one or more procedures and/or features of the one or more treatment services, one or more entities that have past experience with the one or more treatment services, a combination thereof, and/or the like. In a further example, one or more trust disposition values can characterize: the entity's past positive or negative experiences with side-effects and/or adverse health conditions resulting from the chemical compound (e.g., a medicine); and/or future positive and/or negative experiences that the entity expects regarding side-effects and/or adverse health conditions resulting from the chemical compound (e.g., a medicine).

Thus, the assessment component 302 can determine the one or more susceptibility values based on one or more factors associated with side-effects and/or adverse health conditions resulting from a chemical compound (e.g., a medicine), which can be characterized by one or more trust disposition values. For example, the assessment component 302 can determine a low susceptibility disposition value (e.g., indicative that an entity can be less susceptible) towards one or more treatment services based on, for example, one or more trust disposition values characterizing that: an entity can be less likely (e.g., as compared to predefined threshold) to be suffering from side-effects and/or adverse health conditions resulting from a chemical compound (e.g., a medicine); an entity can be less likely (e.g., as compared to predefined threshold) to be responsive to treatment services (e.g., due to a lack of trust in the treatment services); an entity trusts that the side-effects and/or adverse health conditions resulting from a chemical compound (e.g., a medicine) have resulted in and/or will result in positive experiences; a combination thereof, and/or the like. In another example, the assessment component 302 can determine a high susceptibility disposition value (e.g., indicative that an entity can be likely susceptible) towards one or more treatment services based on, for example, one or more trust disposition values characterizing that: an entity can be likely (e.g., as compared to predefined threshold) to be suffering from side-effects and/or adverse health conditions resulting from a chemical compound (e.g., a medicine); an entity can be likely (e.g., as compared to predefined threshold) to be responsive to treatment services (e.g., due to the existence of trust in the treatment services); an entity trusts that the side-effects and/or adverse health conditions resulting from a chemical compound (e.g., a medicine) have resulted in and/or will result in negative experiences; a combination thereof, and/or the like.

The assessment component 302 can assess one or more trust disposition values by comparing the trust disposition values to one or more predefined thresholds to determine their likeliness. Additionally, the assessment component 302 can assess one or more trust disposition values based on (e.g., in response to) assessment of one or more other trust disposition values. For example, the assessment of one or more trust dispositions (e.g., characterizing one or more relationships associated with one or more factors of the susceptibility disposition value) as compared to a predefined threshold can serve as a criterion for the assessment of one or more other trust disposition values (e.g., characterizing one or more other relationships associated with one or more other factors of the susceptibility disposition value).

In one or more embodiments, the assessment component 302 can determine the susceptibility disposition value based on a single factor (e.g., likely responsiveness to treatment services, or a likeliness to be suffering from a side-effect and/or adverse health condition), and thereby the one or more trust disposition values that can characterize the single factor. In one or more other embodiments, the assessment component 302 can determine the susceptibility disposition value based on multiple factors (e.g., likeliness of experiencing a side-effect and/or adverse health condition from a chemical compound, likely responsiveness to treatment services, and/or expected disposition towards the side-effect and/or adverse health condition), and thereby the one or more trust disposition values that can characterize the multiple factors. For example, the susceptibility disposition value can be based on: whether one or more first trust disposition values, which for example can characterize a likelihood that the subject entity is experiencing a side-effect and/or adverse health condition from a chemical compound, meet a defined criterion (e.g., as compared to a predefined threshold); and/or a difference between one or more second trust disposition values, which for example can characterize the subject entity's likely responsiveness to one or more treatment services, and one or more third trust disposition values, which for example can characterize the subject entity's disposition towards the side-effects and/or adverse health conditions caused by the chemical compound (e.g., the medicine).

Figure 4:
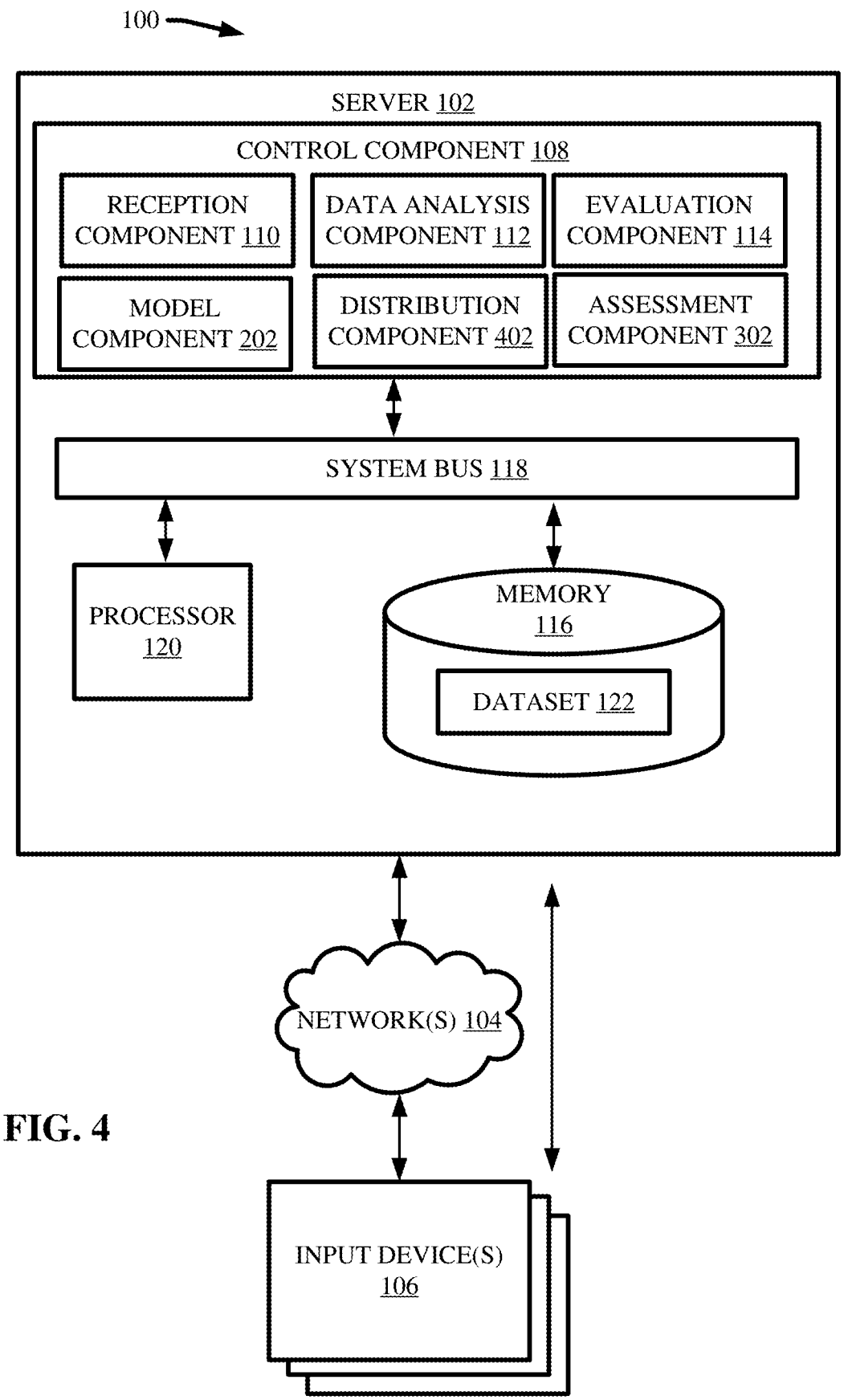
FIG. 4 illustrates a block diagram of an example, non-limiting system that can determine the susceptibility of one or more entities towards one or more treatment services based on at least a determined trust disposition value and/or can distribute the one or more treatment services in accordance with one or more embodiments described herein.

FIG. 4 illustrates a block diagram of the example, non-limiting system 100 further comprising distribution component 402 in accordance with one or more embodiments described herein. Repetitive description of like elements employed in other embodiments described herein is omitted for sake of brevity. The distribution component 402 can facilitate distribution of one or more treatment services to one or more entities based on the one or more susceptibility disposition values. The distribution component 402 can be: located within the server 102, located outside the server 102, and/or a combination thereof (e.g., via implementation of a cloud computing environment).

In one or more embodiments, the assessment component 302 can store determined susceptibility disposition values in one or more susceptibility databases, which can be located in the memory 116 and/or a cloud computing environment. Further, the assessment component 302 can update the one or more susceptibility databases as one or more susceptibility disposition values change based on updated data (e.g., updated trust disposition values computed based on newly received and/or collected data). The distribution component 402 can monitor the one or more susceptibility databases and identify when one or more susceptibility disposition values are greater than or equal to a predefined threshold. In response to identifying a susceptibility disposition value greater than or equal to the predefined threshold, the distribution component 402 can distribute one or more treatment services to one or more entities associated with the subject susceptibility disposition value. For example, the distribution component 402 can distribute one or more treatment services via the one or more networks 104. Further, the distribution component 402 can distribute the one or more treatment services to the one or more input devices 106 to facilitate presentation to the one or more entities. In addition, and/or alternatively, the distribution component 402 can generate one or more recommendations regarding whether to distribute the one or more treatment services to the subject one or more entities based on the one or more susceptibility disposition values. For example, the one or more generated recommendations can: encourage distribution of the one or more treatment services to the one or more entities based on the one or more susceptibility disposition values being greater than or equal to a predefined threshold; or discourage distribution of the one or more treatment services to the one or more entities based on the one or more susceptibility disposition values being lower than a predefined threshold. The generated recommendation (e.g., a message conveyed via text, audio, and/or video) can be sent (e.g., via the one or more networks 104) by the distribution component 402 to one or more medical professionals and/or the one or more entities.

In various embodiments, the assessment component 302 can send a command code (e.g., via the one or more networks 104) to the distribution component 402, thereby instructing the distribution component 402 to facilitate distribution of the one or more treatment services based on the computed susceptibility disposition values. For example, the assessment component 302 can send the command code in response to determining a susceptibility disposition value that is greater than or equal to a predefined threshold. In response to receiving the command code, the distribution component 402 can distribute one or more treatment services to one or more entities associated with the subject susceptibility disposition value. For example, the distribution component 402 can distribute one or more treatment services via the one or more networks 104. Further, the distribution component 402 can distribute the one or more treatment services to the one or more input devices 106 to facilitate presentation to the one or more entities. In addition, and/or alternatively, the command code can instruct the distribution component 402 to generate one or more recommendations regarding whether to distribute the one or more treatment services to the subject one or more entities based on the one or more susceptibility disposition values. For example, the one or more generated recommendations can: encourage distribution of the one or more treatment services to the one or more entities based on the one or more susceptibility disposition values being greater than or equal to a predefined threshold; or discourage distribution of the one or more treatment services to the one or more entities based on the one or more susceptibility disposition values being lower than a predefined threshold. The generated recommendation (e.g., a message conveyed via text, audio, and/or video) can be sent (e.g., via the one or more networks 104) by the distribution component 402 to one or more medical professionals and/or the one or more entities.

Figure 5:
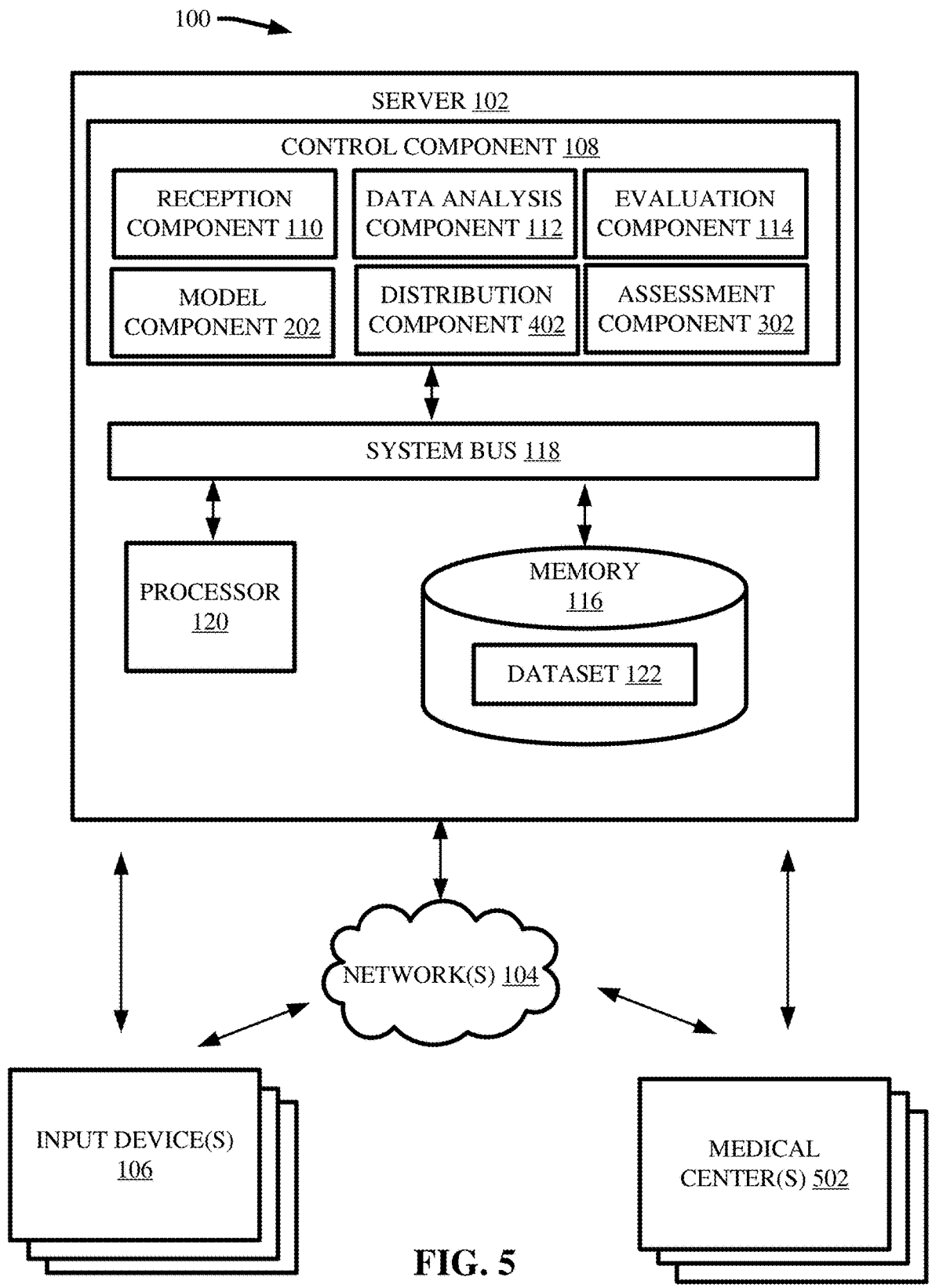
FIG. 5 illustrates a block diagram of an example, non-limiting system that can determine the susceptibility of one or more entities towards one or more treatment services based on at least a trust disposition value and/or one or more medical diagnoses regarding the one or more entities in accordance with one or more embodiments described herein.

FIG. 5 illustrates a block diagram of the example, non-limiting system 100 further comprising one or more medical centers 502 in accordance with one or more embodiments described herein. Repetitive description of like elements employed in other embodiments described herein is omitted for sake of brevity.

As shown in FIG. 5, the server 102 can be operatively coupled (e.g., directly and/or indirectly via the one or more networks 104) to one or more medical centers 502. The one or medical centers 502 can be facilities where medical assistance, medical diagnoses, medical reports, medical therapies, and/or medical treatments can be provided. Example medical centers 502 can include, but are not limited to: hospitals, urgent care clinics, physician practices, nursing homes, a combination thereof, and/or the like. In one or more embodiments, the server 102 (e.g., the control component 108) can receive medical data from the one or more medical centers 502, wherein the medical data can regard a subject entity and can be used by the control component 108 to determine one or more trust disposition values. For example, one or more medical professionals (e.g., physicians) at the one or more medical centers 502 can capture images of a subject individual's brain structure to assess one or more neurological features. As previously described herein, an individual's brain structure can be indicative of the individual's predisposition to an ailment (e.g., pain and/or chronic pain) and/or willingness to trust. The medical data (e.g., one or more brain images and/or medical history) can be sent to the server 102 (e.g., the control component 108) and used (e.g., via the evaluation component 114) to create a predisposition baseline, which can be further augmented based on the other various forms of data described herein.

In various embodiments, the system 100 (e.g., via the control component 108) can autonomously: collect data regarding trust dynamics of an entity (e.g., data regarding communications that indicate the fulfillment or violation of one or more commitments); determine one or trust disposition values based on the collected data; maintain the currency of the one or more trust disposition values using, for example, one or more machine learning technologies; generate one or more trust graphs to predict one or more trust disposition values that can characterize indirect relationships involving the subject entity; determine one or more susceptibility disposition values based on the one or more trust disposition values; and/or distribute one or more treatment services based on the one or more susceptibility disposition values. Therefore, the system 100 tailor one or more treatment services associated to an entity based on recent experience involving the entity that can affect the entity's susceptibility towards the one or more treatment services. Further, the system 100 can determine an entity's susceptibility towards one or more treatment services expeditiously by negating intervention by a medical professional (e.g., a physician). Thus, an individual subject to the analyses and/or evaluations of the system 100 can benefit from up-to-date treatment services distributed during periods of optimal expected effectiveness based on the individual's current disposition of trust.

Figure 6:
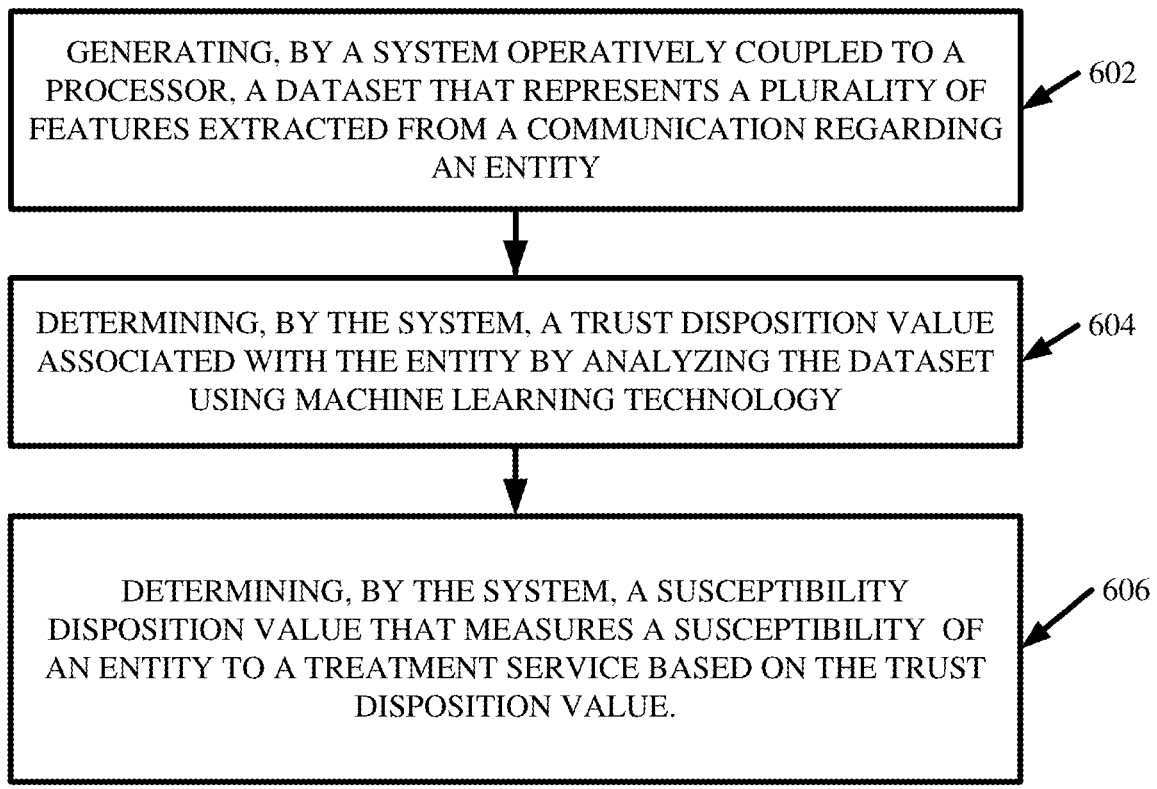
FIG. 6 illustrates a flow diagram of an example, non-limiting method that can facilitate determining the susceptibility of one or more entities towards one or more treatment services based on at least a trust disposition value regarding the one or more entities in accordance with one or more embodiments described herein.

FIG. 6 illustrates a flow diagram of an example, non-limiting method 600 that can facilitate determining one or more susceptibility disposition values that can characterize one or more entities' susceptibility towards one or more treatment services based on one or more computed trust disposition values in accordance with one or more embodiments described herein. Repetitive description of like elements employed in other embodiments described herein is omitted for sake of brevity.

At 602, the method 600 can comprise generating, by a system 100 (e.g., via reception component 110 and/or data analysis component 112) operatively coupled to a processor 120, one or more datasets (e.g., dataset 122) that can represent a plurality of features extracted from one or more communications regarding an entity (e.g., a patient). In one or more embodiments, the one or more communications can be initiated and/or facilitated by one or more AI systems (e.g., one or more chatbots). Additionally, the one or more communications can be accessed via an external source, such as an email account. Further, the one or more communications can regard one or more commitments involving the entity, and/or the one or more extracted features can delineate whether the one or more commitments were fulfilled or violated. Thus, in various embodiments the one or more communications can be indicative of the entity's past positive and/or negative experiences with an individual (e.g., a physician) and/or object (e.g., a medicine and/or medical treatment).

At 604, the method 600 can comprise determining, by the system 100 (e.g., via the data analysis component 112 and/or the evaluation component 114), one or more trust disposition values associated with the entity by analyzing the one or more datasets using machine learning technology. For example, the determining can comprise computing a likelihood that the entity will trust an individual (e.g., a physician) and/or object (e.g., a medicine and/or medical treatment) based on past positive and/or negative experiences. For instance, the system 100 (e.g., via the evaluation component 114) can utilize Equation 1 and/or Equation 2 to compute the one or more trust disposition values.

At 606, the method 600 can comprise determining, by the system 100 (e.g., via the assessment component 302), one or more susceptibility disposition values that can measure a susceptibility of one or more entities to one or more treatment services based on the one or more trust disposition values. For example, the determining at 606 can compare one or more trust disposition values to a predefined threshold and/or to other trust disposition values (e.g., which can also be determined at 604). Further, the determining can be based on one or more factors regarding the one or more entities' susceptibility towards the one or more treatment services, wherein the one or more factors can be characterized by the one or more trust disposition values. Example factors regarding the one or more entities' susceptibility towards the one or more treatment services can include, but are not limited to: a likelihood that the one or more entities are suffering from one or more side-effects and/or adverse health conditions caused by one or more chemical compounds (e.g., medicines); a likelihood the one or more entities will be responsive to one or more treatment services; the one or more entities' expected disposition towards the one or more side-effect and/or adverse health condition; a combination thereof, and/or the like.

Figure 7:
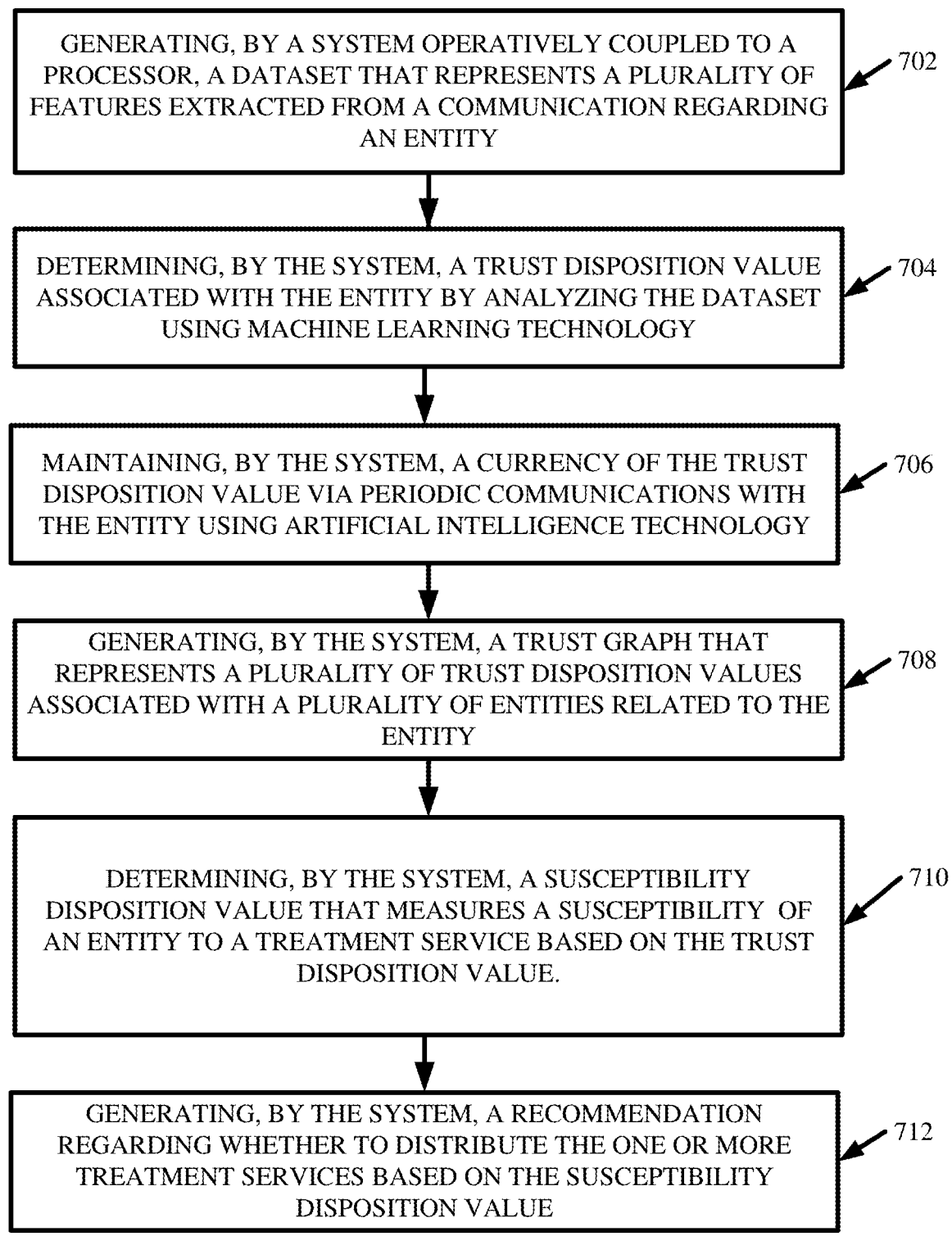
FIG. 7 illustrates a flow diagram of an example, non-limiting method that can facilitate determining the susceptibility of one or more entities towards one or more treatment services based on at least a trust disposition value regarding the one or more entities in accordance with one or more embodiments described herein.

FIG. 7 illustrates a flow diagram of an example, non-limiting method 700 that can facilitate determining one or more susceptibility disposition values that can characterize one or more entities' susceptibility towards one or more treatment services based on one or more computed trust disposition values in accordance with one or more embodiments described herein. Repetitive description of like elements employed in other embodiments described herein is omitted for sake of brevity.

At 702, the method 700 can comprise generating, by a system 100 (e.g., via reception component 110 and/or data analysis component 112) operatively coupled to a processor 120, one or more datasets (e.g., dataset 122) that can represent a plurality of features extracted from one or more communications regarding an entity (e.g., a patient). In one or more embodiments, the one or more communications can be initiated and/or facilitated by one or more AI systems (e.g., one or more chatbots). Additionally, the one or more communications can be accessed via an external source, such as an email account. Further, the one or more communications can regard one or more commitments involving the entity, and/or the one or more extracted features can delineate whether the one or more commitments were fulfilled or violated. Thus, in various embodiments the one or more communications can be indicative of the entity's past positive and/or negative experiences with an individual (e.g., a physician) and/or object (e.g., a medicine and/or medical treatment).

At 704, the method 700 can comprise determining, by the system 100 (e.g., via the data analysis component 112 and/or the evaluation component 114), one or more trust disposition values associated with the entity by analyzing the one or more datasets using machine learning technology. For example, the determining can comprise computing a likelihood that the entity will trust an individual (e.g., a physician) and/or object (e.g., a medicine and/or medical treatment) based on past positive and/or negative experiences. For instance, the system 100 (e.g., via the evaluation component 114) can utilize Equation 1 and/or Equation 2 to compute the one or more trust disposition values.

At 706, the method 700 can comprise maintaining, by the system 100 (e.g., via the reception component 110, the data analysis component 112, and/or the evaluation component 114), a currency (e.g., a currentness) of the one or more trust disposition values via periodic communications with the entity using one or more AI technologies. For example, one or more chatbots (e.g., utilized by the reception component 110) can engage the entity in conversation in predefined intervals (e.g., each day, each week, each month, and/or the like). Further, the one or more trust disposition values can be updated (e.g., via the evaluation component 114) based on new data extracted (e.g., via the data analysis component 112) from the most current conversation with the chatbot.

At 708, the method 700 can comprise generating, by the system 100 (e.g., via the model component 202), one or more trust graphs that can represent a plurality of trust disposition values associated with a plurality of entities related to the entity. The plurality of entities can be in direct relationships with the entity or indirect relationships with the entity (e.g., relationships established through one or more intermediate relationships). The one or more trust graphs can facilitate determining one or more trust disposition values regarding relationships that lack historical data (e.g., lack communications between the subject entities and/or previous commitments between the entities).

At 710, the method 700 can comprise determining, by the system 100 (e.g., via the assessment component 302), one or more susceptibility disposition values that can measure a susceptibility of one or more entities to one or more treatment services based on the one or more trust disposition values. For example, the determining at 710 can compare one or more trust disposition values to a predefined threshold and/or to other trust disposition values (e.g., which can also be determined at 704). Further, the determining can be based on one or more factors regarding the one or more entities' susceptibility towards the one or more treatment services, wherein the one or more factors can be characterized by the one or more trust disposition values. Example factors regarding the one or more entities' susceptibility towards the one or more treatment services can include, but are not limited to: a likelihood that the one or more entities are suffering from one or more side-effects and/or adverse health conditions caused by one or more chemical compounds (e.g., medicines); a likelihood the one or more entities will be responsive to one or more treatment services; the one or more entities' expected disposition towards the one or more side-effect and/or adverse health condition; a combination thereof, and/or the like.

At 712, the method 700 can comprise generating, by the system 100 (e.g., via the control component 108), one or more recommendations regarding whether to distribute the one or more treatment services based on the one or more susceptibility disposition values. The one or more treatment services can regard, for example, one or more chemical effects affecting the one or more entities as a result of consuming one or more chemical compounds (e.g., medicines). For example, the one or more generated recommendations can: encourage distribution of the one or more treatment services to the one or more entities based on the one or more susceptibility disposition values being greater than or equal to a predefined threshold; or discourage distribution of the one or more treatment services to the one or more entities based on the one or more susceptibility disposition values being lower than a predefined threshold. Also, the distribution component 402 can send the one or more generated recommendations to one or more medical professionals via the one or more networks 104. Further, the distribution component 402 can send the one or more generated recommendations to the one or more entities via the one or more networks 104.

Additionally, or alternatively, at 712 the method 700 can comprise distributing (e.g., autonomously), by the system 100 (e.g., via the distribution component 402), the one or more treatment services based on the one or more susceptibility disposition values. The one or more treatment services can regard, for example, one or more chemical effects affecting the one or more entities as a result of consuming one or more chemical compounds (e.g., medicines). For example, the distribution component 402 can send the one or more treatment services to the one or more entities via the one or more networks 104. For instance, the one or more entities can be presented the one or more treatment services via the one or more input devices 106.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
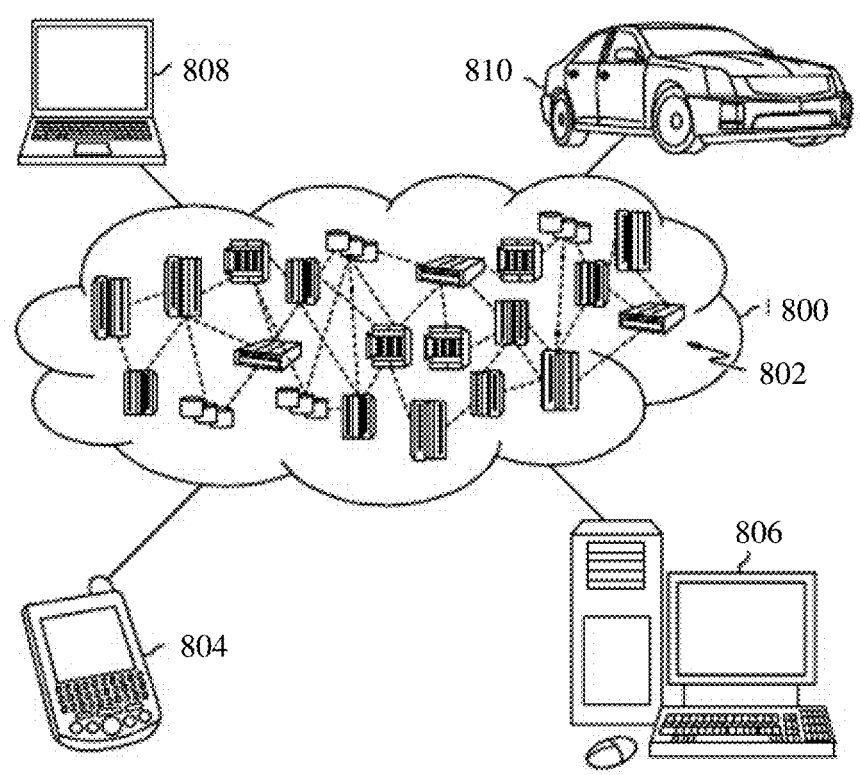
FIG. 8 depicts a cloud computing environment in accordance with one or more embodiments described herein.

Referring now to FIG. 8, illustrative cloud computing environment 800 is depicted. Repetitive description of like elements employed in other embodiments described herein is omitted for sake of brevity. As shown, cloud computing environment 800 includes one or more cloud computing nodes 802 with which local computing devices used by cloud consumers, such as, for example, personal digital assistant (PDA) or cellular telephone 804, desktop computer 806, laptop computer 808, and/or automobile computer system 810 may communicate. Nodes 802 may communicate with one another. They may be grouped (not shown) physically or virtually, in one or more networks, such as Private, Community, Public, or Hybrid clouds as described hereinabove, or a combination thereof. This allows cloud computing environment 800 to offer infrastructure, platforms and/or software as services for which a cloud consumer does not need to maintain resources on a local computing device. It is understood that the types of computing devices 804-810 shown in FIG. 8 are intended to be illustrative only and that computing nodes 802 and cloud computing environment 800 can communicate with any type of computerized device over any type of network and/or network addressable connection (e.g., using a web browser).

Figure 9:
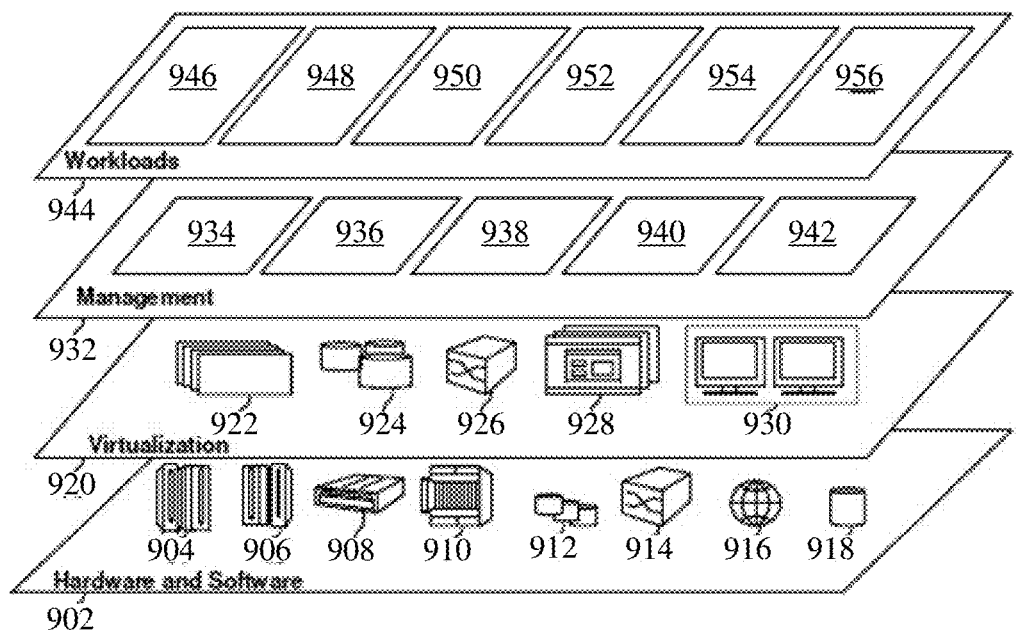
FIG. 9 depicts abstraction model layers in accordance with one or more embodiments described herein.

Referring now to FIG. 9, a set of functional abstraction layers provided by cloud computing environment 800 (FIG. 8) is shown. Repetitive description of like elements employed in other embodiments described herein is omitted for sake of brevity. It should be understood in advance that the components, layers, and functions shown in FIG. 9 are intended to be illustrative only and embodiments of the invention are not limited thereto. As depicted, the following layers and corresponding functions are provided.

Hardware and software layer 902 includes hardware and software components. Examples of hardware components include: mainframes 904; RISC (Reduced Instruction Set Computer) architecture based servers 906; servers 908; blade servers 910; storage devices 912; and networks and networking components 914. In some embodiments, software components include network application server software 916 and database software 918.

Virtualization layer 920 provides an abstraction layer from which the following examples of virtual entities may be provided: virtual servers 922; virtual storage 924; virtual networks 926, including virtual private networks; virtual applications and operating systems 928; and virtual clients 930.

In one example, management layer 932 may provide the functions described below. Resource provisioning 934 provides dynamic procurement of computing resources and other resources that are utilized to perform tasks within the cloud computing environment. Metering and Pricing 936 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 938 provides access to the cloud computing environment for consumers and system administrators. Service level management 940 provides cloud computing resource allocation and management such that required service levels are met. Service Level Agreement (SLA) planning and fulfillment 942 provide pre-arrangement for, and procurement of, cloud computing resources for which a future requirement is anticipated in accordance with an SLA.

Workloads layer 944 provides examples of functionality for which the cloud computing environment may be utilized. Examples of workloads and functions which may be provided from this layer include: mapping and navigation 946; software development and lifecycle management 948; virtual classroom education delivery 950; data analytics processing 952; transaction processing 954; and assessing an entity's susceptibility to a treatment service 956. Various embodiments of the present invention can utilize the cloud computing environment described with reference to FIGS. 8 and 9 to determine a trust disposition value associated with one or more entities and/or determine the susceptibility of the one or more entities to one or more treatment services based on the trust disposition value.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

Figure 10:
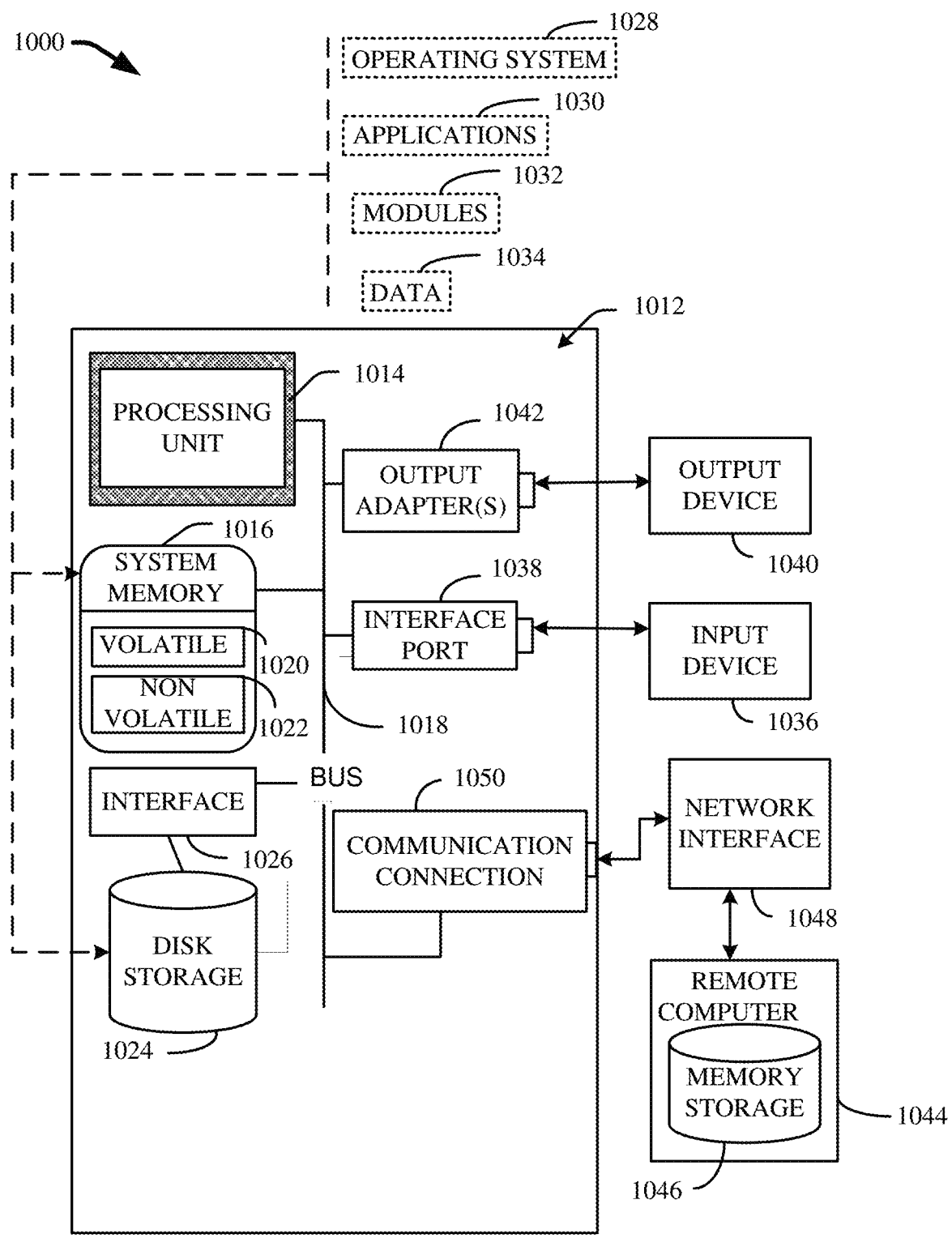
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure can include a computer 1012. The computer 1012 can also include a processing unit 1014, a system memory 1016, and a system bus 1018. The system bus 1018 can operably couple system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, can be stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface can be used, such as interface 1026. FIG. 10 also depicts software that can act as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 can take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through one or more input devices 1036. Input devices 1036 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1014 through the system bus 1018 via one or more interface ports 1038. The one or more Interface ports 1038 can include, for example, a serial port, a parallel port, a game port, and a universal serial bus (USB). One or more output devices 1040 can use some of the same type of ports as input device 1036. Thus, for example, a USB port can be used to provide input to computer 1012, and to output information from computer 1012 to an output device 1040. Output adapter 1042 can be provided to illustrate that there are some output devices 1040 like monitors, speakers, and printers, among other output devices 1040, which require special adapters. The output adapters 1042 can include, by way of illustration and not limitation, video and sound cards that provide a means of connection between the output device 1040 and the system bus 1018. It should be noted that other devices and/or systems of devices provide both input and output capabilities such as one or more remote computers 1044.

Computer 1012 can operate in a networked environment using logical connections to one or more remote computers, such as remote computer 1044. The remote computer 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer 1044. Remote computer 1044 can be logically connected to computer 1012 through a network interface 1048 and then physically connected via communication connection 1050. Further, operation can be distributed across multiple (local and remote) systems. Network interface 1048 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components;
   a processor, operably coupled to the memory, and that executes the computer executable components stored in the memory, wherein the computer executable components comprise:
      an assessment component that determines a susceptibility disposition value that measures a susceptibility of a patient to a treatment service based on a trust disposition value, wherein the trust disposition value characterizes an amount of trust the patient has in an entity associated with the treatment service and is determined based on a communication between the patient and a chatbot using machine learning technology;
      a model component that generates a computer model that represents a plurality of trust disposition values associated with a plurality of entities that are related to the patient and that is traversable algorithmically and facilitate predicting the trust disposition value; and
      a distribution component that generates a recommendation regarding whether to perform the treatment service based on the susceptibility disposition value, the computer model depicting linkages between the plurality of entities and medicines and medical treatments through the plurality of trust disposition values, the linkages depicting how the patient is indirectly correlated with the plurality of entities and the medicines or the medical treatments.

2. The system of claim 1, further comprising:
   a data collection component that generates a dataset that represents a plurality of features extracted from the communication; and
   an evaluation component that determines the trust disposition value associated with the patient by analyzing the dataset using the machine learning technology.

3. The system of claim 2, wherein the susceptibility disposition value is further based on a second trust disposition value, wherein the evaluation component predicts the second trust disposition value based on the trust graph, and wherein the second trust disposition value characterizes an amount of trust the patient has in a second entity.

4. The system of claim 2, wherein the communication regards a commitment regarding the patient, and wherein the plurality of features delineates whether the commitment was fulfilled.

5. The system of claim 1, wherein the treatment service regards a chemical effect affecting the entity.

6. The system of claim 5, wherein the chemical effect is a chemically induced dependency generated by a chemical compound.

7. The system of claim 5, wherein the distribution component sends the recommendation to the patient.

8. The system of claim 1, further comprising:
   a distribution component that distributes the treatment service to the patient based on a comparison of the susceptibility disposition value to a predefined threshold.

9. The system of claim 1, wherein the susceptibility disposition value is determined in a cloud computing environment.

10. A computer-implemented method, comprising:
   determining, by a system operatively coupled to a processor, a susceptibility disposition value that measures a susceptibility of a patient to a treatment service based on a trust disposition value, wherein the trust disposition value characterizes an amount of trust the patient has in an entity associated with the treatment service and is determined based on a communication between the patient and a chatbot using machine learning technology;
   generating, by the system, a computer model that represents a plurality of trust disposition values associated with a plurality of entities that are related to the patient and that is traversable algorithmically and facilitates predicting the trust disposition value; and
   generating, by the system, a recommendation regarding whether to perform the treatment service based on the susceptibility disposition value, the computer model depicting linkages between the plurality of entities and medicines and medical treatments through the plurality of trust disposition values, the linkages depicting how the patient is indirectly correlated with the plurality of entities and the medicines or the medical treatments.

11. The computer-implemented method of claim 10, further comprising:
   generating, by the system, a dataset that represents a plurality of features extracted from the communication regarding the entity; and
   determining, by the system, the trust disposition value associated with the patient by analyzing the dataset using the machine learning technology.

12. The computer-implemented method of claim 10, wherein the treatment service regards a chemical effect affecting the entity.

13. The computer-implemented method of claim 10, further comprising:

distributing, by the system, the treatment service to the patient based on a comparison of the susceptibility disposition value to a predefined threshold value.

14. The computer-implemented method of claim 13, wherein the treatment service is a media selected from a group consisting of a text, a video and an audio signal.

15. A computer program product for assessing a treatment service, the computer program product comprising a computer readable storage medium having program instructions embodied therewith, the program instructions executable by a processor to cause the processor to:
   determine, by the processor, a susceptibility disposition value that measures a susceptibility of a patient to the treatment service based on a trust disposition value, wherein the trust disposition value characterizes an amount of trust the patient has in an entity associated with the treatment service and is determined based on a communication between the patient and a chatbot using machine learning technology;
   generate, by the processor, a computer model that represents a plurality of trust disposition values associate with a plurality of entities and that is traversable algorithmically and facilitates predicting the trust disposition value; and
   generate, by the processor, a recommendation regarding whether to perform the treatment service based on the susceptibility disposition value, the computer model depicting linkages between the plurality of entities and medicines and medical treatments through the plurality of trust disposition values, the linkages depicting how the patient is indirectly correlated with the plurality of entities and the medicines or the medical treatments.

16. The computer program product of claim 15, wherein the program instructions further cause the processor to:
   generate, by the processor, a dataset that represents a plurality of features extracted from the communication regarding the entity; and
   determine, by the processor, the trust disposition value associated with the patient by analyzing the dataset using the machine learning technology.

17. The computer program product of claim 15, wherein the treatment service regards a chemical effect affecting the entity.

18. The computer program product of claim 15, wherein the trust disposition value is determined in a cloud computing environment.

* * * * *